United States Patent
Dixit

(10) Patent No.: US 10,482,991 B2
(45) Date of Patent: Nov. 19, 2019

(54) SYSTEMS AND METHODS FOR SAMPLING AND ANALYSIS OF POLYMER CONFORMATIONAL DYNAMICS

(71) Applicant: ZYMEWORKS INC., Vancouver (CA)

(72) Inventor: Surjit Bhimarao Dixit, Richmond (CA)

(73) Assignee: ZYMEWORKS INC., Vancouver (CA)

(*) Notice: Subject to any disclaimer, the term of this patent is extended or adjusted under 35 U.S.C. 154(b) by 0 days.

(21) Appl. No.: 14/421,490

(22) PCT Filed: Aug. 16, 2013

(86) PCT No.: PCT/CA2013/050637
§ 371 (c)(1),
(2) Date: Feb. 13, 2015

(87) PCT Pub. No.: WO2014/026296
PCT Pub. Date: Feb. 20, 2014

(65) Prior Publication Data
US 2015/0220681 A1    Aug. 6, 2015

Related U.S. Application Data

(60) Provisional application No. 61/684,236, filed on Aug. 17, 2012.

(51) Int. Cl.
| | | |
|---|---|---|
| *G16B 5/00* | (2019.01) | |
| *G06F 17/10* | (2006.01) | |
| *G16B 15/00* | (2019.01) | |
| *G16C 10/00* | (2019.01) | |

(52) U.S. Cl.
CPC .......... *G16B 5/00* (2019.02); *G06F 17/10* (2013.01)

(58) Field of Classification Search
None
See application file for complete search history.

(56) References Cited

U.S. PATENT DOCUMENTS

| | | |
|---|---|---|
| 2010/0250217 A1 | 9/2010 | Wang et al. |
| 2011/0053261 A1 | 3/2011 | Lario et al. |
| 2014/0025345 A1 | 1/2014 | Ishiguro |

FOREIGN PATENT DOCUMENTS

| | | |
|---|---|---|
| CA | 2391987 | 5/2001 |
| WO | WO 2002/079784 | 10/2002 |

OTHER PUBLICATIONS

Adcock McCammon, 2006, "Molecular dynamics: survey of methods for simulating the activity of proteins," Chem Rev 106 (5):1589-615.
Desmet et al., 1992, "The dead-end elimination theorem and its use in protein side-chain positioning," Nature 356 (6369):539-542.
Guarnieri and Still, 1994, "A rapidly convergent simulation method: Mixed Monte Carlo/stochastic dynamics," J Comput Chem 15 (11):1302-1310.
Hagen et al., 2007, "Serial replica exchange.", J Phys Chem B 111 (6):1416-23.
Holm and Sander, 1992, "Fast and simple Monte Carlo algorithm for side chain optimization in proteins: application to model building by homology," Proteins 14 (2):213-23.
Jones, 1994, "De novo protein design using pairwise potentials and a genetic algorithm," Protein Sci 3 (4):567-74.
Kono and Doi, 1994, "Energy minimization method using automata network for sequence and side-chain conformation prediction from given backbone geometry," Proteins 19 (3):244-55.
Lazaridis and Karplus, 1999, "Effective energy function for proteins in solution," Proteins: Structure, Function, and Genetics 35: 133-152.
Lee and Subbiah, 1991, "Prediction of protein side-chain conformation by packing optimization," J Mol Biol 217 (2):373-88.
Smock and Gierasch, 2009, "Sending signals dynamically," Science 324 (5924): 198-203.
Flores and Gerstein, "Predicting protein ligand binding motions with the conformation explorer." *BMC Bioinformatics*, 12:417 (2011).

*Primary Examiner* — Michael L Borin
(74) *Attorney, Agent, or Firm* — Morgan, Lewis & Bockius LLP; Brett Lovejoy

(57) ABSTRACT

Systems and methods for searching conformation space of a polymer to determine a three-dimensional conformation of the polymer that satisfies a performance metric is provided. The polymer comprises a plurality of domains and at least a first hinge. Initial three-dimensional coordinates of the polymer are altered by pivoting the first domain with respect to the second domain about the first hinge thereby obtaining an altered set of three-dimensional coordinates for the polymer. In this altering, atoms within the first domain are held fixed with respect to each other and atoms within the second domain are also held fixed with respect to each other. The altered set of coordinates is scored against a performance metric. Additional instances of the altering and scoring are performed, if necessary, until the altered set of three-dimensional coordinates satisfy the performance metric.

44 Claims, 19 Drawing Sheets

```
zapp hinge_sampling --plib=$PLIB --rlib=$RLIB \
--struct=structures/
albu1_nc_prime_bivalent_linked_4.azdb \
--sample-region="(residue.chain_id=A and
residue.seq_id >=334 and residue.seq_id <= 350)
or (residue.chain_id=B and residue.seq_id >= 255
and residue.seq_id <= 270)" \
--moving-region="(residue.chain_id=A and
residue.seq_id >=334 and residue.seq_id <= 350)
or (residue.chain_id=B and residue.seq_id >= 255
and residue.seq_id <= 270) or (residue.chain_id=A
and residue.seq_id >= 351) or (residue.chain_id=B
and residue.seq_id <= 254)" \
--sidechain-region="residue in [A/352, A/378, A/
547, A/547, A/450, A/293, A/290, A/294, A/333, A/
297, B/314, B/371, B/307, B/311, B/225, B/224, B/
150, B/149]" \
--steps=1000 \
--temperature=500 \
--snapshot-frequency=1 \
--out-structure=tas.azdb \
--out-trajectory=tas.nc \
--rand-seed=1 \
--debug
```

Fig. 18

```
zapp hinge_sampling --plib=$PLIB --
rlib=$RLIB \
--struct=../structures/IIIaF.azdb \
--region-type="carbohydrate" \
--sample-region="GLYCAM and not
hydrogen" \
--moving-region="GLYCAM" \
--sidechain-
region="residue.chain_id=A" \
--steps=1000 \
--temperature=20000 \
--snapshot-frequency=1 \
--sample-probability=1 \
--sidechain-probability=0 \
--out-structure=tas.azdb \
--out-trajectory=tas.nc \
--rand-seed=1 \
--debug
```

Fig. 19

SYSTEMS AND METHODS FOR SAMPLING AND ANALYSIS OF POLYMER CONFORMATIONAL DYNAMICS

CROSS REFERENCE TO RELATED APPLICATION

This application claims priority to U.S. Provisional Application No. 61/684,236, filed Aug. 17, 2012, which is hereby incorporated by reference herein in its entirety.

TECHNICAL FIELD

The invention provides systems and methods for searching the conformation space of a polymer to determine a three-dimensional conformation of the polymer that satisfies a performance metric.

BACKGROUND

Polymers are highly dynamic molecules and many of their functionally important characteristics, such as affinity for substrates and stability of active form, depend on an ensemble of the structures comprising multiple conformational sub-states, their probabilities and transition rates, and characteristics of the intrinsic free energy surface.

In the case of proteins, there is growing evidence indicating that binding of a protein to particular targets is often associated with a preferential selection of one or more of these conformations. See Smock and Gierasch, 2009, "Sending signals dynamically," Science 324 (5924): 198-203.

Detailed structural information obtained using experimental procedures such as X-ray crystallography does not provide much information on a polymer's dynamic behavior. An understanding of polymer dynamics is especially important in studies of environmental and solvent effects on stability and macromolecular association, processes that are often accompanied by structural reorganization.

In order to develop a broader understanding of how polymers function, and to develop better industrial and pharmaceutical polymers, it is necessary to develop an appreciation for these diverse conformational states. Traditionally, conformational sampling of polymer structures is carried out using deterministic or stochastic simulation approaches. See Adcock McCammon, 2006, "Molecular dynamics: survey of methods for simulating the activity of proteins," Chem Rev 106 (5):1589-615.

In a deterministic approach, such as molecular dynamics simulation, Newtonian mechanics is employed to calculate the trajectory of all the particles in the system as a result of the interaction forces acting between them. In this procedure, the atomic displacements are estimated at very short time-steps, and numerical integration is carried out in an iterative computation to predict the detailed system dynamics over longer time-scales. There is an upper limit to the time-step that can be used, and this, together with the large size of the polymer system being studied, computationally limits the length of the simulation that can be performed. This in turn limits the number of large-scale conformational transitions and hence the number of sub-states of the polymer that can be revealed in the course of a single trajectory. Although these traditional computational simulations address the dynamic character of polymers, molecular dynamic approaches (deterministic) are computationally intense, making them impractical for studying slow conformational changes of larger polymers, such as large proteins.

In a stochastic approach, such as Monte Carlo sampling, a number of variables in the system are randomly selected and perturbed to generate a new configuration of the system. In an evolved version of the algorithm, such as the Metropolis Monte Carlo method, the new configuration is accepted or rejected on the basis of an energetic criterion at the temperature of interest, leading to a Boltzmann weighted ensemble of thermodynamically relevant configurations. The use of Monte Carlo sampling can result in significantly more efficient jumps between relevant conformational states, thus overcoming the barriers observed in traditional molecular dynamics simulations. But selecting the degrees of freedom that, when perturbed, would result in a workable acceptance probability under the Metropolis scheme is often a major problem in the application of this approach. In other words, simulations based on purely stochastic algorithms such as the Metropolis Monte-Carlo technique have not been successful in solving this problem because they tend to yield limited acceptance ratios resulting in inefficient simulation. Methods which include stochastic moves with deterministic MD evolution have been discussed but have been limited in their application. See, Guarnieri and Still, 1994, "A rapidly convergent simulation method: Mixed Monte Carlo/stochastic dynamics," J Comput Chem 15 (11):1302-1310; and U.S. Pat. No. 5,740,072.

Given the above background, improved systems and method of arriving at polymer conformational information is therefore needed.

SUMMARY OF THE PRESENT DISCLOSURE

An approach to the issue of conformational sampling of a polymer has been developed using insight from a high-level or coarse-grain model of the polymer and heuristic analysis of the polymer's structure, to infer the location of domains, loops, and hinge regions. Based on this analysis, specific large-scale conformational changes and the associated conformational states of the polymer are predicted. Detailed atomistic simulations are then performed to develop a refined understanding of the conformational states. This reveals the conformational and energetic landscape of the polymer.

Thus, in one aspect, methods of sampling conformational states of a polymer using a computer system are provided in which a coarse-grain modelling of the polymer is performed to generate an altered conformation and then an atomistic simulation of the altered conformation is performed. In some embodiments, the coarse-grain modelling comprises performing a stochastic computational method, such as, for example, Monte Carlo. In some embodiments, the atomistic simulation comprises performing a deterministic computational method, such as, for example, molecular dynamics.

The systems and methods described herein provide for rapid generation and analysis of multiple potentially important polymer conformational states. Deterministic and stochastic search methods are combined in a way that offers improved conformational sampling of polymers compared to the use of either of these two techniques by themselves. The disclosed systems and methods incorporate the strength of coarse grain models and heuristic knowledge of polymers to predict hinge locations on a polymer, Monte Carlo moves to introduce large-scale conformational changes and combines them with the strength of a Molecular Dynamics simulation to provide detailed information on the conformational flexibility around a structural substrate. The disclosed systems and methods provide for finding diverse polymer conformations and their relative populations concurrently, leading to surprising speed and practicality of modeling in light of previous methods and solutions.

One aspect of the present disclosure provides a method of searching the conformation space of a polymer to determine a three-dimensional conformation of the polymer that satisfies a performance metric. The method comprises, at a computer system having one or more processors and memory storing one or more programs to be executed by the one or more processors, obtaining an initial set of three-dimensional coordinates $\{x_{1A\_init}, \ldots, x_{NA\_init}, x_{1B\_init}, \ldots, x_{MB\_init}, x_{1C\_init}, \ldots, x_{PC\_init}, \ldots\}$ for the polymer. The polymer comprises a plurality of domains. Each respective $x_{iA}$ in $\{x_{1A\_init}, \ldots, x_{NA\_init}, x_{1B\_init}, \ldots, x_{MB\_init}, x_{1C\_init}, \ldots, x_{PC\_init}, \ldots\}$ is a three dimensional coordinate for an atom in a first domain in the plurality of domains. Each respective $x_{iB}$ in $\{x_{1A\_init}, \ldots, x_{NA\_init}, x_{1B\_init}, \ldots, x_{MB\_init}, x_{1C\_init}, \ldots, x_{PC\_init}, \ldots\}$ is a three dimensional coordinate for an atom in a second domain in the plurality of domains. Each respective $x_{iC}$ in $\{x_{1A\_init}, \ldots, x_{NA\_init}, x_{1B\_init}, \ldots, x_{MB\_init}, x_{1C\_init}, \ldots, x_{PC\_init}, \ldots\}$ is a three dimensional coordinate for an atom in a first hinge of the polymer. The polymer is characterized by an ability for the first and second domain to pivot with respect to each other about the first hinge. The three-dimensional coordinates of the polymer are altered by pivoting the first domain with respect to the second domain about the first hinge thereby obtaining an altered set of three-dimensional coordinates $\{x_{1A\_alt}, \ldots, x_{NA\_alt}, x_{1B\_alt}, \ldots, x_{MB\_alt}, x_{1C\_alt}, \ldots, x_{PC\_alt}, \ldots\}$ for the polymer. During this altering step, atoms within the first domain are held fixed with respect to each other and atoms within the second domain are held fixed with respect to each other. The altered set of coordinates is scored against the performance metric. Additional instances of the altering and scoring are performed until the altered set of three-dimensional coordinates $\{x_{1A\_alt}, \ldots, x_{NA\_alt}, x_{1B\_alt}, \ldots, x_{MB\_alt}, x_{1C\_alt}, \ldots, x_{PC\_alt}, \ldots\}$ satisfy the performance metric.

In some embodiments, prior to the initial altering step, a determination is made as to which residues of the polymer are in the first domain, first hinge, and the second domain.

In some embodiments, the polymer comprises a plurality of hinges. This plurality of hinges includes the first hinge. For each respective hinge in the plurality of hinges, there is a corresponding pair of domains in the plurality of domains that pivot with respect to each other about the respective hinge. In some such embodiments, the method further comprises, prior to the altering step, determining the identity of the residues in each hinge in the plurality of hinges. In some embodiments, this information is already known. In some embodiments, the altering further pivots a third domain with respect to a fourth domain in the plurality of domains about a second hinge in the plurality of hinges. In so doing, atoms within the third domain are held fixed with respect to each other and atoms within the fourth domain are held fixed with respect to each other.

In some embodiments, the scoring comprises solving a loop closure problem for the first hinge to concurrently introduce alterations to some or all of a plurality of hinge parameters associated with the first hinge. In some embodiments, fewer than 2(n−2) hinge parameters are altered in the loop closure problem. In some embodiments n is the number of residues in the first hinge.

In some embodiments, the location of the first hinge is determined by subjecting the initial set of three-dimensional coordinates to normal mode analysis, principal component analysis, covariance analysis, protein domain analysis, rigidity analysis, sequence feature analysis.

In some embodiments, determining the identity of the residues in each hinge in the plurality of hinges comprises subjecting the initial set of three-dimensional coordinates to normal mode analysis, principal component analysis, covariance analysis, protein domain analysis, rigidity analysis, sequence feature analysis.

In some embodiments, the polymer is a protein and the altering further comprises repacking protein side chain geometries in the alternate set of three-dimensional coordinates by applying a protein packing algorithm. In some embodiments, the protein packing algorithm optimizes side chain rotamer geometry for amino acids in the protein that are displaced by the altering step.

In some embodiments, the performance metric comprises a physics-based energy function. In some embodiments, the performance metric comprises a knowledge-based energy function.

In some embodiments, the altering and scoring are performed sequentially in time and wherein an $n^{th}$ instance of the altering alters the altered set of coordinates of the polymer from either the $n^{th}-1$ or the $n^{th}-2$ instance of the altering. This selection of the altered set of coordinates of the polymer for the $n^{th}$ instance of the altering is on the basis of the Metropolis criteria, and n is a positive integer of three or greater.

In some embodiments, the polymer is a protein, the first hinge comprises a plurality of residues, each residue in the plurality of residues is associated with a backbone torsion angle in a plurality of backbone torsion angles, and the pivoting the first domain with respect to the second domain comprises biasing respective backbone torsion angles in the plurality of backbone torsion angles towards stereochemically acceptable dihedral states.

In some embodiments, the method further comprises performing a molecular dynamics simulation of the altered set of three-dimensional coordinates prior to the scoring. In some embodiments, this molecular dynamics simulation comprises using an explicit or implicit solvent model. In some embodiments, this molecular dynamics simulation is a serial replica exchange (SRE) molecular dynamics simulation. In some embodiments, the SRE molecular dynamics simulation comprises temperature tempering or solvent tempering.

In some embodiments, the scoring comprises calculating a free energy landscape based on the altered set of three-dimensional coordinates by using a method selected from the group consisting of Umbrella Sampling, Thermodynamic Integration, Free Energy Perturbation, Adaptive Biasing Force based potential of mean force calculations and targeted molecular dynamics.

In some embodiments, a plurality of instances of the altering is performed thereby generating a plurality of altered sets of three-dimensional coordinates.

In some embodiments, the polymer is a protein and the protonation state of an ionizable amino acid side chain in the polymer varies among the plurality of altered sets of three-dimensional coordinates.

In some embodiments, the method further comprises assigning each altered set of three-dimensional coordinates in the plurality of altered sets of three-dimensional coordinates to one of a plurality of conformational clusters. The assigning step comprises clustering based on structural data of the plurality of altered sets of three-dimensional coordinates selected from the group consisting of an inter-domain geometric parameter, an inter-atomic contact pattern, a radius of gyration, a solvent accessibility and root mean square deviation.

In some embodiments, a plurality of instances of the altering are performed concurrently thereby obtaining a plurality of altered sets of three-dimensional coordinates for the polymer. In some such embodiments, the method further comprises concurrently performing a separate independent molecular dynamics simulation of each altered set of three-dimensional coordinates in the plurality of altered sets of three-dimensional coordinates. In this way, a plurality of independent molecular dynamics simulations is performed, prior to the scoring step. In some embodiments, the plurality of independent molecular dynamics simulations is performed in parallel (a) on nodes of a computer cluster, (b) in a distributed computing system or (c) by general purpose computing on graphics processing units. In some embodiments, when a conformational similarity between intermediate structures in any two of the plurality of independent molecular dynamics simulations is within a predetermined threshold, one of the two molecular dynamics simulations is terminated. In some embodiments, an independent molecular dynamics simulation in the plurality of independent molecular dynamics simulation comprises adaptively computing an energy distribution of a plurality of conformations of the polymer.

In some embodiments, the altering biases the altered set of three-dimensional coordinates toward a principal low frequency mode of motion using principal component analysis of a molecular dynamics trajectory or anisotropic elastic network model analysis.

In some embodiments, the polymer is characterized by a primary sequence of residues and the residues in the first hinge are from different portions of the primary sequence that are interrupted by portions of the primary sequence that are in the first domain or the second domain.

In some embodiments, the polymer is a polynucleic acid, a polyribonucleic acid, a polysaccharide, or a polypeptide. In some embodiments, the polymer comprises thirty or more residues, forty or more residues, fifty or more residues, or one or more residues. In some embodiments, the first hinge comprises five or more residues, ten or more residues, fifteen or more residues, or twenty or more residues.

In some embodiments, the polymer is a protein, the first hinge comprises a plurality of residues, each residue in the plurality of residues is associated with a backbone torsion angle in a plurality of backbone torsion angles, the pivoting the first domain with respect to the second domain comprises biasing respective backbone torsion angles in the plurality of backbone torsion angles towards stereochemically acceptable dihedral states, and the polymer is characterized by a primary sequence of residues. The residues in the first hinge are from different portions of the primary sequence that are interrupted by portions of the primary sequence that are in the first domain or the second domain.

In some embodiments, the altering and the scoring are performed using a Monte Carlo approach.

In some embodiments, the polymer is a protein, the first hinge comprises n residues, where n is a positive integer of 2 or greater, the first hinge comprises $2(n-2)$ backbone dihedral angles, a subset of the $2(n-2)$ backbone dihedral angles in the first hinge are not altered during the altering step, and the altering step and the scoring step are performed using a Monte Carlo approach.

In some embodiments, the method further comprises refining the altered set of three-dimensional coordinates $\{x_{1A\_alt}, \ldots, x_{NA\_alt}, x_{1B\_alt}, \ldots, x_{MB\_alt}, x_{1C\_alt}, \ldots, x_{PC\_alt}, \ldots\}$ using molecular dynamics.

In some embodiments, the scoring is performed using a potential energy function. In some embodiments, the scoring is performed using a knowledge-based energy function.

Another aspect of the present disclosure provides a computer system for searching the conformation space of a polymer to determine a three-dimensional conformation of the polymer that satisfies a performance metric, the computer system comprising at least one processor and memory storing at least one program for execution by the at least one processor, the memory further comprising instructions for executing the method of any of the methods disclosed herein.

Another aspect of the present disclosure provides a non-transitory computer readable storage medium storing one or more computational modules for searching the conformation space of a polymer to determine a three-dimensional conformation of the polymer that satisfies a performance metric, the one or more computational modules collectively comprising instructions for performing any of the methods disclosed herein.

BRIEF DESCRIPTION OF THE DRAWINGS

The embodiments disclosed herein are illustrated by way of example, and not by way of limitation, in the figures of the accompanying drawings. Like reference numerals refer to corresponding parts throughout the drawings.

FIG. 18 is an example of a script for zapp hinge sampling in accordance with an exemplary embodiment.

FIG. 19 is an exemplary script used to evaluate a polymer in accordance with an exemplary embodiment.

DETAILED DESCRIPTION

Disclosed are methods of altering an input conformation of a polymer to generate an altered conformation of the polymer in a computer system. One aspect provides a method of altering an input conformation of a polymer to generate an altered conformation of the polymer in a computer system, in which the polymer comprises (i) a plurality of amino acids and (ii) a hinge characterized by a hinge parameter, the method comprising (a) determining the location of the hinge and (b) applying an alteration of the hinge parameter, thereby generating the altered conformation of the polymer.

Figure 1:
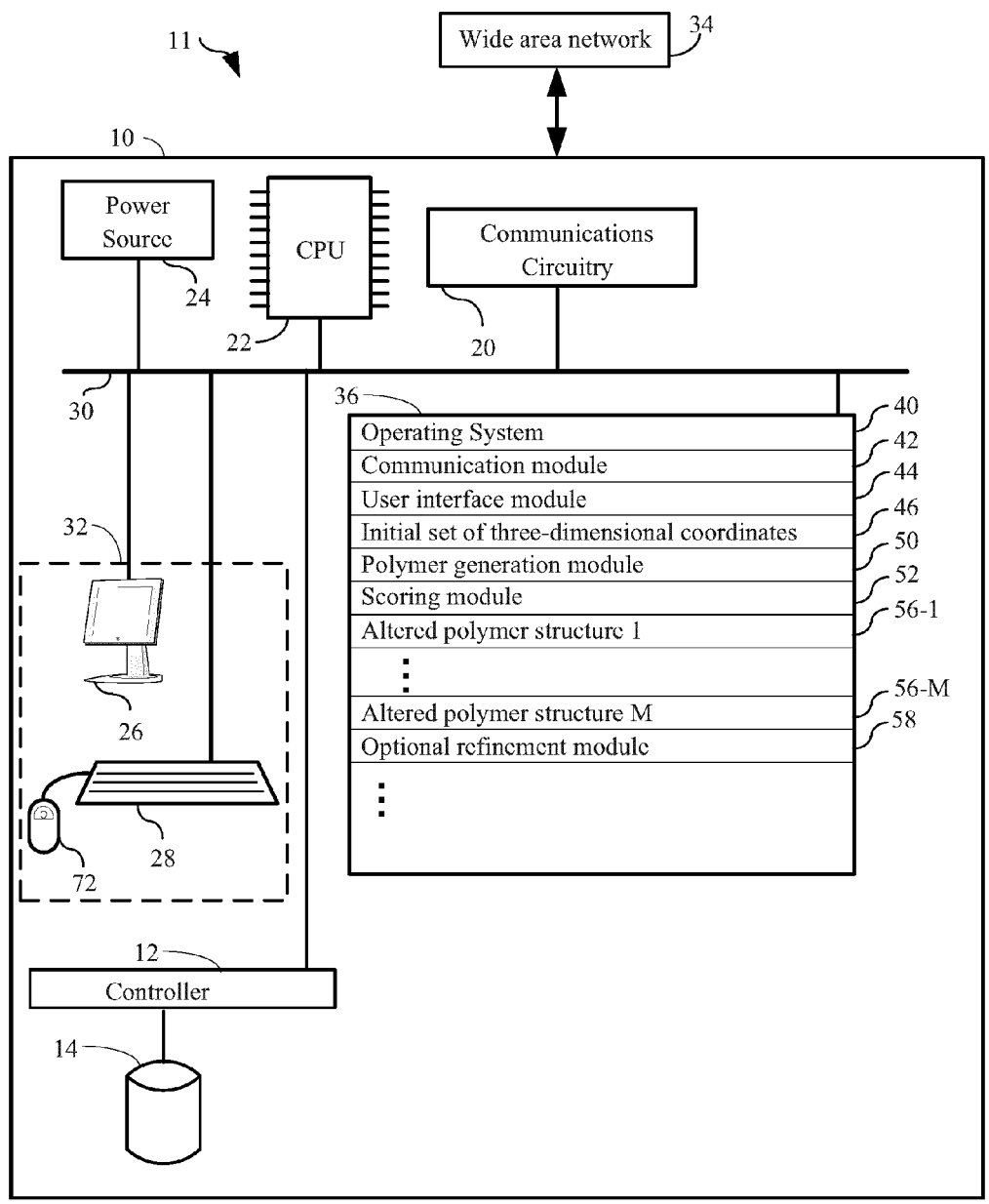
FIG. 1 is a block diagram illustrating a system, according to an exemplary embodiment of the present disclosure.

The following provides systems and methods of searching the conformation space of a polymer to determine a three-dimensional conformation of the polymer that satisfies a performance metric. FIG. 1 is a block diagram illustrating a system 11 in accordance with one such embodiment. System 11 comprises a computer 10 that typically includes one or more processing units (CPUs, sometimes called processors) 22 for executing programs (e.g., programs stored in memory 36), one or more network or other communications interfaces 20, memory 36, a user interface 32, which includes one or more input devices (such as a keyboard 28, mouse 72, touch screen, keypads, etc.) and one or more output devices such as a display device 26, and one or more communication buses 30 for interconnecting these components. The communication buses 30 may include circuitry (sometimes called a chipset) that interconnects and controls communications between system components.

Memory 36 includes high-speed random access memory, such as DRAM, SRAM, DDR RAM or other random access solid state memory devices; and typically includes non-volatile memory, such as one or more magnetic disk storage devices, optical disk storage devices, flash memory devices, or other non-volatile solid state storage devices. Memory 36 optionally includes one or more storage devices remotely located from the CPU(s) 22. Memory 36, or alternately the non-volatile memory device(s) within memory 36, comprises a non-transitory computer readable storage medium. In some embodiments, memory 36 or the computer readable storage medium of memory 36 stores the following programs, modules and data structures, or a subset thereof:

- an operating system 40 that includes procedures for handling various basic system services and for performing hardware dependent tasks;
- an optional communication module 42 that is used for connecting the computer 10 to other computers via the one or more communication interfaces 20 (wired or wireless) and one or more communication networks 34, such as the Internet, other wide area networks, local area networks, metropolitan area networks, and so on;
- an optional user interface module 42 that receives commands from the user via the input devices 28, 72, etc. and generates user interface objects in the display device 26;
- an initial set of three-dimensional coordinates $\{x_{1A\_init}, x_{NA\_init}, x_{1B\_init}, \ldots, x_{MB\_init}, x_{1C\_init}, \ldots, x_{PC\_init}, \ldots\}$ 46 for the polymer under study comprising a plurality of atoms, in which each respective $x_{iA}$ in $\{x_{1A\_init}, \ldots, x_{NA\_init}, x_{1B\_init}, \ldots, x_{MB\_init}, x_{1C\_init}, \ldots, x_{PC\_init}, \ldots\}$ is a three dimensional coordinate for an atom in a first domain in a plurality of domains, each respective $x_{iB}$ in $\{x_{1A\_init}, \ldots, x_{NA\_init}, x_{1B\_init}, \ldots, x_{MB\_init}, x_{1C\_init}, \ldots, x_{PC\_init}, \ldots\}$ is a three dimensional coordinate for an atom in a second domain in the plurality of domains, each respective $x_{iC}$ in $\{x_{1A\_init}, \ldots, x_{NA\_init}, x_{1B\_init}, \ldots, x_{MB\_init}, x_{1C\_init}, \ldots, x_{PC\_init}, \ldots\}$ is a three dimensional coordinate for an atom in a first hinge of the polymer, in which the polymer is characterized by an ability for the first and second domain to pivot with respect to each other about the first hinge;
- a polymer generation module 50 that comprises instructions for altering three-dimensional coordinates of the polymer by pivoting the first domain with respect to the second domain about the first hinge thereby obtaining an altered set of three-dimensional coordinates $\{x_{1A\_alt}, \ldots, x_{NA\_alt}, x_{1B\_alt}, \ldots, x_{MB\_alt}, x_{1C\_alt}, \ldots, x_{PC\_alt}, \ldots\}$ for the polymer;
- a scoring module 52 for scoring the altered set of coordinates against the performance metric;
- a plurality of altered three-dimensional coordinates 56 for the molecular system, where typically each altered structure 56 has the same atoms as the molecular system under study but has different structural coordinates; and
- an optional refinement module 58 for refining one or more of the altered polymer structures 56 using molecular dynamics.

In some embodiments, the polymer comprises between 2 and 5,000 residues, between 20 and 50,000 residues, more than 30 residues, more than 50 residues, or more than 100 residues. In some embodiments, a residue in the polymer comprises two or more atoms, three or more atoms, four or more atoms, five or more atoms, six or more atoms, seven or more atoms, eight or more atoms, nine or more atoms or ten or more atoms. In some embodiments the polymer 44 has a molecular weight of 100 Daltons or more, 200 Daltons or more, 300 Daltons or more, 500 Daltons or more, 1000 Daltons or more, 5000 Daltons or more, 10,000 Daltons or more, 50,000 Daltons or more or 100,000 Daltons or more.

A polymer, such as those that can be studied using the disclosed systems and methods, is a large molecular system composed of repeating structural units. These repeating structural units are termed particles or residues interchangeably herein. In some embodiments, each particle $p_i$ in the set of $\{p_1, \ldots, p_K\}$ particles represents a single different residue in the native polymer. To illustrate, consider the case where the native comprises 100 residues. In this instance, the set of $\{p_1, \ldots, p_K\}$ comprises 100 particles, with each particle in $\{p_1, \ldots, p_K\}$ representing a different one of the 100 particles.

In some embodiments, the polymer that is evaluated using the disclosed systems and methods is a natural material. In some embodiments, the polymer is a synthetic material. In some embodiments, the polymer is an elastomer, shellac, amber, natural or synthetic rubber, cellulose, Bakelite, nylon, polystyrene, polyethylene, polypropylene, or polyacrylonitrile, polyethylene glycol, or polysaccharide.

In some embodiments, the polymer is a heteropolymer (copolymer). A copolymer is a polymer derived from two (or more) monomeric species, as opposed to a homopolymer where only one monomer is used. Copolymerization refers to methods used to chemically synthesize a copolymer. Examples of copolymers include, but are not limited to, ABS plastic, SBR, nitrile rubber, styrene-acrylonitrile, styrene-isoprene-styrene (SIS) and ethylene-vinyl acetate. Since a copolymer consists of at least two types of constituent units (also structural units, or particles), copolymers can be classified based on how these units are arranged along the chain. These include alternating copolymers with regular alternating A and B units. See, for example, Jenkins, 1996, "Glossary of Basic Terms in Polymer Science," Pure Appl. Chem. 68 (12): 2287-2311, which is hereby incorporated herein by reference in its entirety. Additional examples of copolymers are periodic copolymers with A and B units arranged in a repeating sequence (e.g. (A-B-A-B-B-A-A-A-A-B-B-B)). Additional examples of copolymers are statistical copolymers in which the sequence of monomer residues in the copolymer follows a statistical rule. If the probability of finding a given type monomer residue at a particular point in the chain is equal to the mole fraction of that monomer residue in the chain, then the polymer may be referred to as a truly random copolymer. See, for example, Painter, 1997, *Fundamentals of Polymer Science*, CRC Press, 1997, p 14, which is hereby incorporated by reference herein in its entirety. Still other examples of copolymers that may be evaluated using the disclosed systems and methods are block copolymers comprising two or more homopolymer subunits linked by covalent bonds. The union of the homopolymer subunits may require an intermediate non-repeating subunit, known as a junction block. Block copolymers with two or three distinct blocks are called diblock copolymers and triblock copolymers, respectively.

In some embodiments, the polymer is in fact a plurality of polymers, where the respective polymers in the plurality of polymers do not all have the molecular weight. In such embodiments, the polymers in the plurality of polymers fall into a weight range with a corresponding distribution of chain lengths. In some embodiments, the polymer is a branched polymer molecular system comprising a main chain with one or more substituent side chains or branches. Types of branched polymers include, but are not limited to, star polymers, comb polymers, brush polymers, dendronized polymers, ladders, and dendrimers. See, for example, Rubinstein et al., 2003, *Polymer physics*, Oxford; New York: Oxford University Press. p. 6, which is hereby incorporated by reference herein in its entirety.

In some embodiments, the polymer is a polypeptide. As used herein, the term "polypeptide" means two or more amino acids or residues linked by a peptide bond. The terms "polypeptide" and "protein" are used interchangeably herein and include oligopeptides and peptides. An "amino acid," "residue" or "peptide" refers to any of the twenty standard structural units of proteins as known in the art, which include imino acids, such as proline and hydroxyproline. The designation of an amino acid isomer may include D, L, R and S. The definition of amino acid includes nonnatural amino acids. Thus, selenocysteine, pyrrolysine, lanthionine, 2-aminoisobutyric acid, gamma-aminobutyric acid, dehydroalanine, ornithine, citrulline and homocysteine are all considered amino acids. Other variants or analogs of the amino acids are known in the art. Thus, a polypeptide may include synthetic peptidomimetic structures such as peptoids. See Simon et al., 1992, Proceedings of the National Academy of Sciences USA, 89, 9367, which is hereby incorporated by reference herein in its entirety. See also Chin et al., 2003, Science 301, 964; and Chin et al., 2003, Chemistry & Biology 10, 511, each of which is incorporated by reference herein in its entirety.

The polypeptides evaluated in accordance with some embodiments of the disclosed systems and methods may also have any number of posttranslational modifications. Thus, a polypeptide includes those that are modified by acylation, alkylation, amidation, biotinylation, formylation, γ-carboxylation, glutamylation, glycosylation, glycylation, hydroxylation, iodination, isoprenylation, lipoylation, cofactor addition (for example, of a heme, flavin, metal, etc.), addition of nucleosides and their derivatives, oxidation, reduction, pegylation, phosphatidylinositol addition, phosphopantetheinylation, phosphorylation, pyroglutamate formation, racemization, addition of amino acids by tRNA (for example, arginylation), sulfation, selenoylation, ISGylation, SUMOylation, ubiquitination, chemical modifications (for example, citrullination and deamidation), and treatment with other enzymes (for example, proteases, phosphotases and kinases). Other types of posttranslational modifications are known in the art and are also included.

In some embodiments, the polymer is an organometallic complex. An organometallic complex is chemical compound containing bonds between carbon and metal. In some instances, organometallic compounds are distinguished by the prefix "organo-" e.g. organopalladium compounds. Examples of such organometallic compounds include all Gilman reagents, which contain lithium and copper. Tetracarbonyl nickel, and ferrocene are examples of organometallic compounds containing transition metals. Other examples include organomagnesium compounds like iodo(methyl) magnesium MeMgI, diethylmagnesium ($Et_2Mg$), and all Grignard reagents; organolithium compounds such as n-butyllithium (n-BuLi), organozinc compounds such as diethylzinc ($Et_2Zn$) and chloro(ethoxycarbonylmethyl)zinc ($ClZ_nCH_2C(=O)OEt$); and organocopper compounds such as lithium dimethylcuprate ($Li^+[CuMe_2]^-$). In addition to the traditional metals, lanthanides, actinides, and semimetals, elements such as boron, silicon, arsenic, and selenium are considered form organometallic compounds, e.g. organoborane compounds such as triethylborane ($Et_3B$).

In some embodiments, the initial set of three-dimensional coordinates 46 for the polymer is obtained by x-ray crystallography, nuclear magnetic resonance spectroscopic techniques, or electron microscopy. In some embodiments, the set of M three-dimensional coordinates $\{x_1, \ldots, x_M\}$ is obtained by modeling (e.g., molecular dynamics simulations).

In some embodiments, the polymer includes two different types of polymers, such as a nucleic acid bound to a polypeptide. In some embodiments, the polymer includes two polypeptides bound to each other. In some embodiments, the polymer under study includes one or more metal ions (e.g. a metalloproteinase with one or more zinc atoms) and/or is bound to one or more organic small molecules (e.g., an inhibitor). In such instances, the metal ions and or the organic small molecules may be represented as one or more additional particles $p_i$ in the set of $\{p_1, \ldots, p_K\}$ particles representing the native polymer.

In some embodiments the polymer under study is a protein. The basic structural elements of proteins are well-known in the art. Nonterminal amino acids typically have the structure —NH—$C^\alpha$HR—CO—, where R represents an amino acid side chain as is known in the art. Atoms such as N, $C^\alpha$, $C^\circ$ and O that are not in the sidechain represent backbone atoms. Atoms of the sidechain, especially the heteroatoms of the sidechain, are referred to as "terminal" atoms. Thus, terminal atoms include $C^\beta$ in alanine, $S^\gamma$ in cysteine, and $N^{\epsilon 1}$ and $C^{\eta 1}$ in tryptophan, for example. Such terminal atoms can be unique. C-alpha or $C^\alpha$ is the carbon atom in the center of each amino acid. The protein backbone includes N, C-alpha, C and O atoms. The backbone dihedral angles of proteins are called $\phi$ (phi, involving the backbone atoms C'—N—$C^\alpha$—C'), $\psi$ (psi, involving the backbone atoms N—$C^\alpha$—C'—N) and $\omega$ (omega, involving the backbone atoms $C^\alpha$—C'—N—$C^\alpha$). Thus, $\phi$ controls the C'—C' distance, $\psi$ controls the N—N distance and $\omega$ controls the $C^\alpha$—$C^\alpha$ distance. The planarity of the peptide bond usually restricts $\psi$ to be 180° (the typical trans case) or 0° (the rare cis case). The sidechain dihedral angles tend to cluster near 180°, 60°, and −60°, which are called the trans, gauche+, and gauche− conformations. The choice of sidechain dihedral angles is affected by the neighbouring backbone and sidechain dihedrals. A Ramachandran map (Ramachandran, Ramakrishnan, and Sasisekharan 1963) is a representation of the stereochemically allowed protein backbone geometries as a function of their variable torsion angles. The method allows for the classification of protein backbone conformations as being allowed, partially allowed or disallowed on the basis of these geometric parameters.

There are different levels of describing the structure of a protein. Primary structure refers to the linear sequence of amino acids that make up the polypeptide chain. The bond between two amino acids is a peptide bond. The sequence of amino acids determines the positioning of the different R groups relative to each other. This positioning determines the way that the protein folds and the final structure of the molecule. The secondary structure of protein molecules refers to the formation of a regular pattern of twists or kinks of the polypeptide chain. The regularity is due to hydrogen bonds forming between the atoms of the amino acid backbone of the polypeptide chain. The two most common types of secondary structure are called the "α-helix" and "β-pleated sheet". Tertiary structure refers to the three dimensional globular structure formed by bending and twisting of the polypeptide chain. This process often means that the linear sequence of amino acids is folded into a compact globular structure. The folding of the polypeptide chain is stabilized by multiple weak, noncovalent interactions. These interactions include hydrogen bonds, electrostatic interactions, hydrophobic interactions, and sometimes covalent bonds. Quaternary structure refers to the fact that some proteins contain more than one polypeptide chain, adding an additional level of structural organization: the association of the polypeptide chains. Each polypeptide chain in the protein is called a subunit. The subunits can be the same polypeptide chain or different ones. For example, the enzyme β-galactosidase is a tetramer, meaning that it is composed of four subunits, and, in this case, the subunits are identical—each polypeptide chain has the same sequence of amino acids. Hemoglobin, the oxygen carrying protein in the blood, is also a tetramer but it is composed of two polypeptide chains of one type (141 amino acids) and two of a different type (146 amino acids).

A polymer is generally understood to exhibit some degree of mobility. As a result, at any given point, a polymer may exist in one of a number of "conformations", "conformational states" or "conformers", that is, in one of a number of different geometric configurations having the same structural formula or connectivity. The term "altered conformation" as used herein refers to a conformation that results from performing the methods disclosed herein on a starting or input conformation. In some instances the polymer is a protein and one conformation comprises a rotamer of an amino acid while another conformation comprises a different rotamer of the same amino acid. The term "rotamer" refers to a combination of torsion angles describing the geometry of an amino acid side chain.

The disclosed methods may also be used to model a "system," which generally comprises a polymer and may further comprise other molecular entities such as solvents, ions and the like. Modeling of the polymer itself could be, without limitation, atomistic or coarse grained.

In some embodiments, the programs or modules identified in FIG. 1 correspond to sets of instructions for performing a function described herein. The sets of instructions can be executed by one or more processors (e.g., the CPUs 22). The above identified modules or programs (e.g., sets of instructions) need not be implemented as separate software programs, procedures or modules, and thus various subsets of these programs or modules may be combined or otherwise re-arranged in various embodiments. In some embodiments, memory 36 stores a subset of the modules and data structures identified above. Furthermore, memory 36 may store additional modules and data structures not described above.

Figure 2:
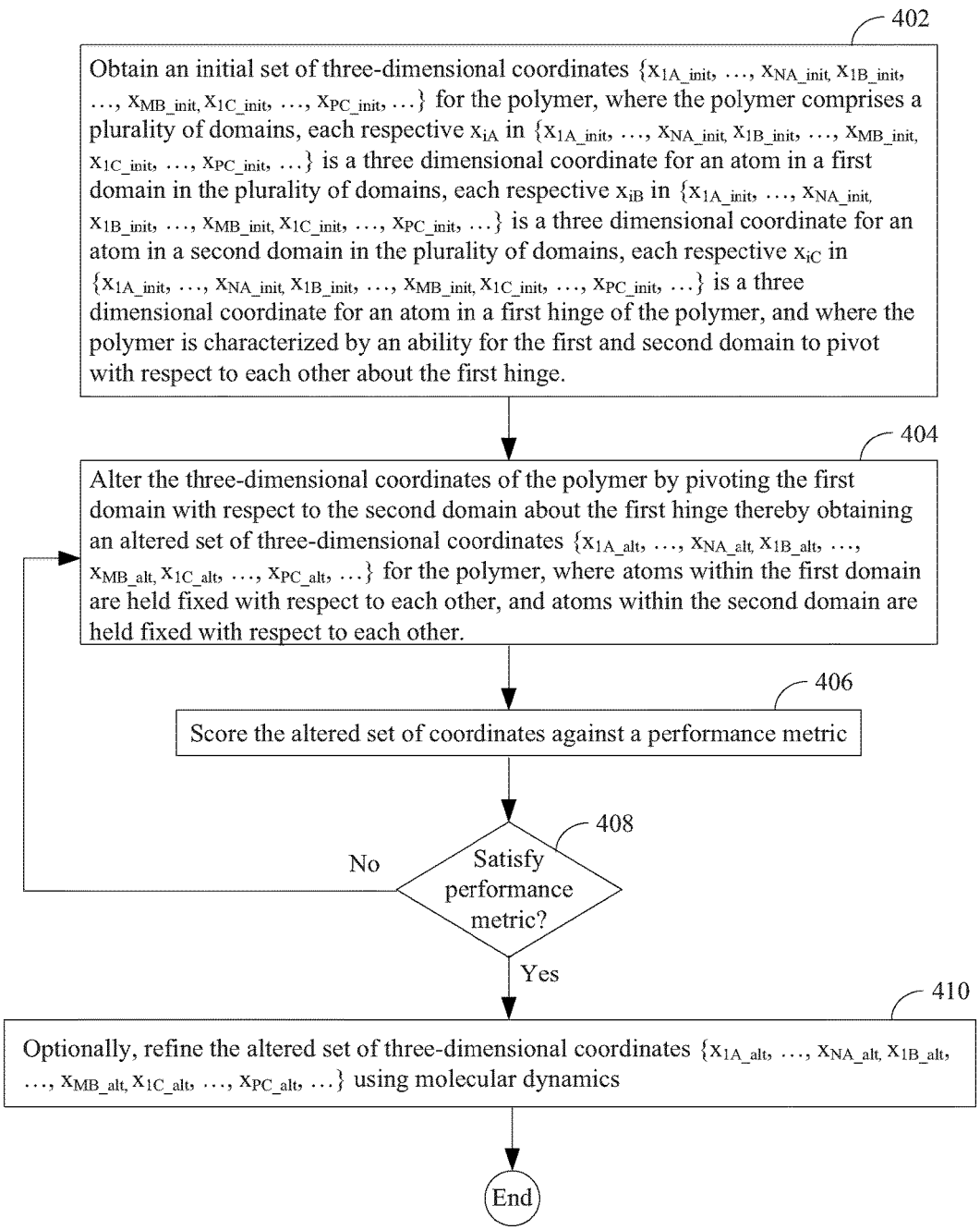
FIG. 2 illustrates a method of searching the conformation space of a polymer to determine a three-dimensional conformation of the polymer that satisfies a performance metric in accordance with an embodiment of the present disclosure.
Figure 3:
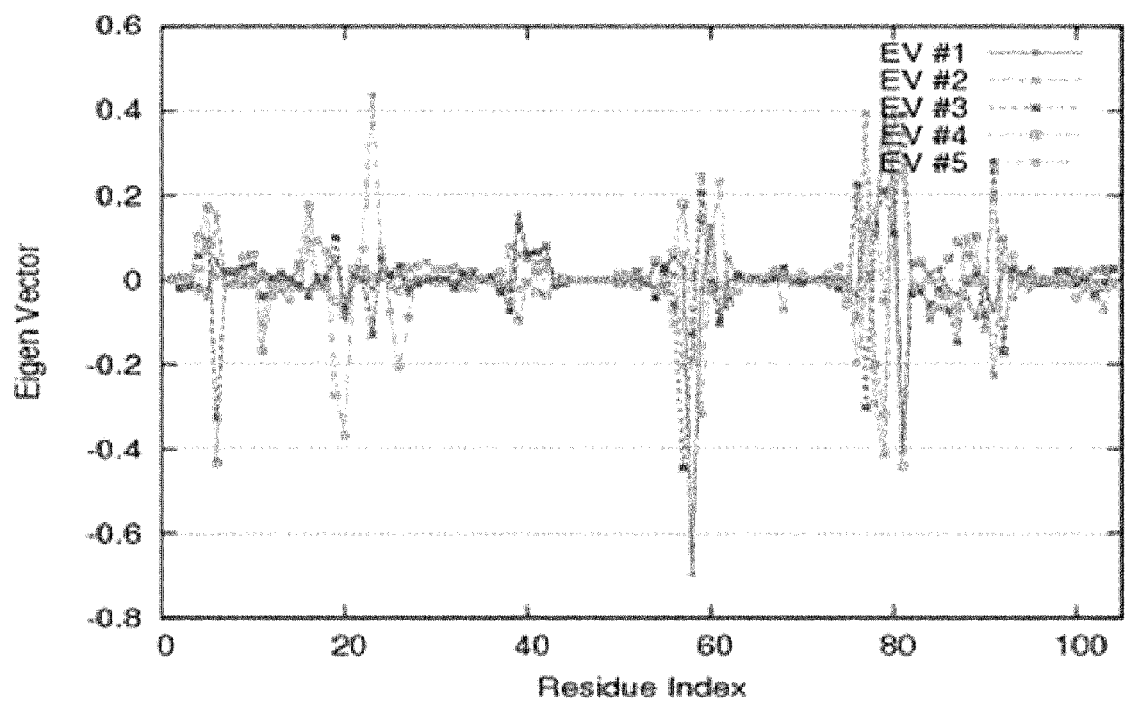
FIGS. 3 and 4 show a graphical representation of the directional information for the residues in a protein with regard to the different modes of motion derived from normal mode analysis. When adjacent residues have the same direction, their move is concerted as a group. When the direction changes sign between neighboring residues, it indicates a junction between two domains moving in different directions and a potential hinge. The magnitudes of the displacement components are used to calibrate the significance of various positions as potential hinges.

Now that a system in accordance with the systems and methods of the present disclosure has been described, attention turns to FIG. 2 which illustrates an exemplary method in accordance with the present disclosure.

Step 402. The residues of a polymer can be characterized according to their degree of mobility. For example, certain amino acids, including those found in secondary structural motifs such as α-helices and β-sheets, can be characterized as being rigid, while other amino acids, such as those in the loops connecting these motifs, can be characterized as being mobile.

Large scale movements in a polymer can sometimes be classified as a hinge movement. A "hinge movement" involves rotation of protein parts (e.g., domains) about a "hinge" or a "hinge region", which refer to one or more mobile residues. Mobile residues tend to exhibit a wider distribution of conformations across an ensemble of polymer conformations, while rigid residues tend to exhibit a narrower distribution.

Accordingly, in step 402 an initial set of three-dimensional coordinates $\{x_{1A\_init}, \ldots, x_{NA\_init}, x_{1B\_init}, \ldots, x_{MB\_init}, x_{1C\_init}, \ldots, x_{PC\_init}, \ldots\}$ for a polymer is obtained, where the polymer comprises a plurality of domains, each respective $x_{iA}$ in $\{x_{1A\_init}, \ldots, x_{NA\_init},$ $x_{1B\_init}, \ldots, x_{MB\_init}, x_{1C\_init}, \ldots, x_{PC\_init}, \ldots\}$ is a three dimensional coordinate for an atom in a first domain in the plurality of domains, each respective $x_{iB}$ in $\{x_{1A\_init}, \ldots, x_{NA\_init}, x_{1B\_init}, \ldots, x_{MB\_init}, x_{1C\_init}, \ldots, x_{PC\_init}, \ldots\}$ is a three dimensional coordinate for an atom in a second domain in the plurality of domains, and each respective $x_{iC}$ in $\{x_{1A\_init}, \ldots, x_{NA\_init}, x_{1B\_init}, \ldots, x_{MB\_init}, x_{1C\_init}, \ldots, x_{PC\_init}, \ldots\}$ is a three dimensional coordinate for an atom in a first hinge of the polymer, wherein the polymer is characterized by an ability for the first and second domain to pivot with respect to each other about the first hinge. This represents the minimum characteristics of the polymer. The polymer may comprise any number of domains and any number of hinges.

A hinge usually involves several residues that undergo significant concurrent conformational changes, while the residues of the rotating portions of the polymer that are not in the hinge remain unchanged relative to the other amino acids in their respective domains. In a polymer, there may be points of directional change along the primary sequence which result in inter-domain geometry necessary for structure or enzymatic activity. They form regions of relative constraint in terms of molecular motion. In many instances, a loop, a linker or a portion thereof can be characterized as a "hinge" or a "hinge region."

Figure 4:
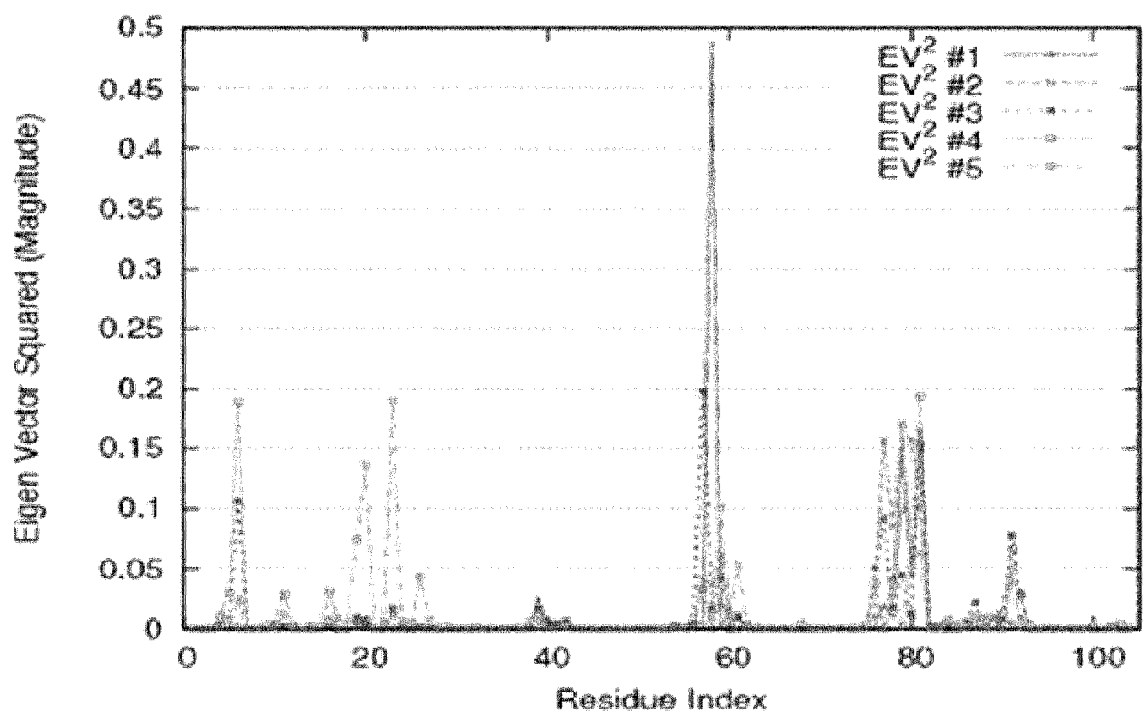
Figure 5:
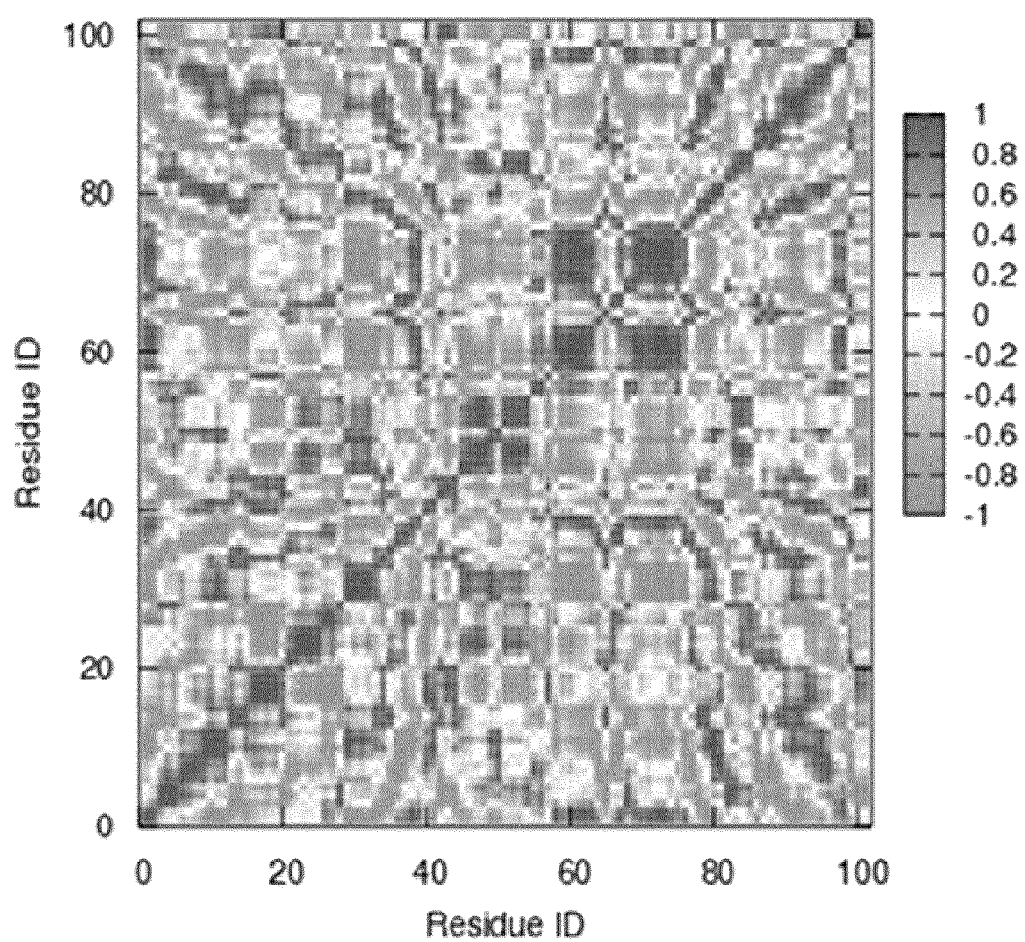
FIG. 5 shows an example of covariance information, which may be derived from Elastic Network Model, Principal Component Analysis (PCA) or Dynamic Cross-Correlation Map (DCCM) methods. The covariance information provided by these methods can be used to identify potential hinges.
Figure 6:
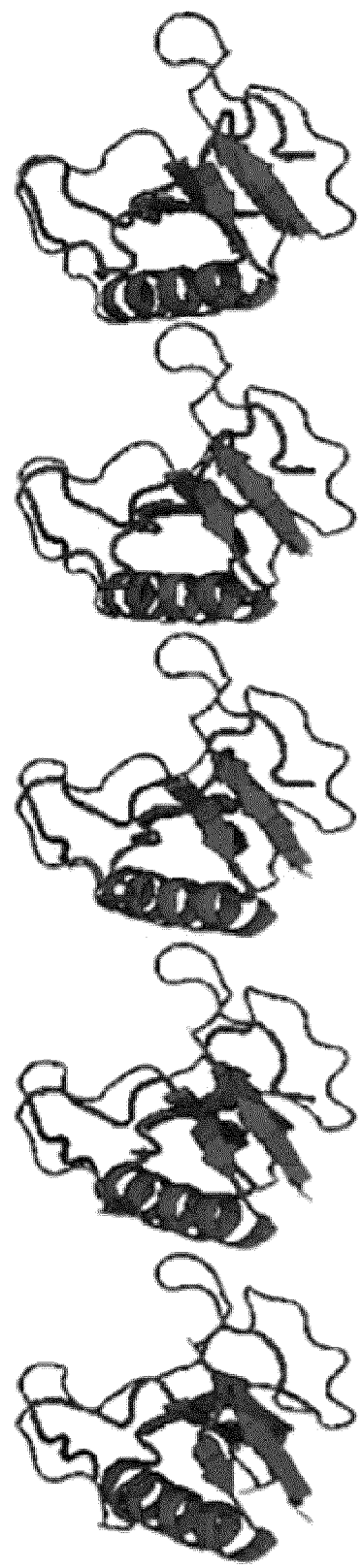
FIG. 6 shows an illustration of predicted potential hinge positions (light shading) mapped onto the sequence of a protein example (Ribonuclease: PDB ID 1BU4). The five images represent the hinges predicted in the five lowest frequency modes of motion for this protein as identified by GNM analysis.

In some embodiments, a hinge comprises residues that are relatively distant in sequence but close in space. For example, the antibody IgG1 structure (FIG. 4) is composed of a homodimeric structure, with each of the monomeric units being composed of a heavy chain with four domains and a light chain with two domains. The dimeric IgG structure is broadly classified into one Fc (fragment crystallizable) and two Fab (fragment antigen binding) sections. Each of the Fab sections is connected to the Fc by a linker of fifteen amino acids and this linker is traditionally referred to as the hinge in the Ab structure. The flexibility achieved in the IgG structure due to the hinge is thought to be important for the functional effectiveness of the Ab molecule. As another example, glutamine binding protein (PDB ID 1ggg and 1wdn) may be considered to have two rigid parts that are connected by two hinge residues 87 and 183. While sequentially separated by 95 residues, the $C_\alpha$ atoms of residues 87 and 183 are about 6 Å apart. Thus, in some embodiments, a hinge region comprises a set of spatially clustered endpoints of a rigid portion of a polymer. Surveys of crystallographically solved structures that evidence domain movements in proteins have revealed hinge and shear motions as basic elements that produce the movements. See Gerstein, Lesk, and Chothia, 1994, "Structural mechanisms for domain movements in proteins," Biochemistry 33 (22):6739-49, which is hereby incorporated by reference.

The hinges of a polymer can also be determined by an analysis selected from the group consisting of normal mode analysis, principal component analysis, covariance analysis, protein domain analysis, rigidity analysis and sequence feature analysis. In some embodiments, normal mode analysis of a coarse grain model is employed in the prediction of hinges. In some embodiment the hinge may be defined on the basis of solvent accessibility and contacts made by the residues. Hinge residues are usually solvent accessible and make minimal contact with rest of the protein domains.

Normal mode analysis (NMA) examines the vibrational and thermal properties of molecular structures at the atomic level. See Bahar and Rader, 2005, "Coarse-grained normal mode analysis in structural biology," Curr Opin Struct Biol 15(5): 586-592, which is hereby incorporated by reference. This method provides analytical solutions to describe the principal modes of motion, also referred to as "normal modes", for a structure around its equilibrium state, characterized by differences in frequency. Since the method describes protein motion around an equilibrium position, it cannot provide the direct insight into the various conformational substates of the protein, or the transitions between them, that molecular dynamics or Monte Carlo simulations can. However, the method provides insight into the low frequency motion characteristics of the system, information that can be used to define polymer domains and the hinges connecting the domains in the polymer structure. Performing NMA on larger molecules is computationally challenging because the equilibrium motion of the molecule needs to be described by a force constant matrix derived from the second derivative of the potential with respect to the Cartesian coordinates.

Elastic Network Models treat the polymer like in NMA but describe the polymer as a set of particles that are interconnected by a network of elastic springs See Bahar, Atilgan, and Erman, 1997, "Direct evaluation of thermal fluctuations in proteins using a single-parameter harmonic potential," Fold Des 2 (3):173-81, which is hereby incorporated by reference. The models employed are simpler than the models employed in NMA. Depending on the granularity of the model, the particles can correspond to atoms in the protein or coarse grain representative points such as C-alpha atom positions in the protein chain, side chain positions or alternate atom group definitions. The models can be employed to describe the structural fluctuations around a stable conformation of a protein. These fluctuations are isotropic in a Gaussian Network Model (see Haliloglu et al., 1997, "Gaussian Dynamics of Folded Proteins," Physical Review Letters 79 (16):3090, which is hereby incorporated by reference herein in its entirety) and anisotropic in the case of Anisotropic Network Model (see Atilgan et al., 2001, "Anisotropy of fluctuation dynamics of proteins with an elastic network model," Biophys J 80 (1):505-15, which is hereby incorporated by reference herein in its entirety).

Principal component analysis (PCA) is a mathematical procedure that reduces a number of correlated variables into a fewer uncorrelated variables called "principal components". The first principal component is selected such that it accounts for as much of the variability in the data as possible, and each succeeding component accounts for as much of the remaining variability as possible. The purpose of PCA is to discover or to reduce the dimensionality of the data set, and to identify new meaningful underlying variables.

PCA is accomplished by establishing actual data in a covariance matrix or a correlation matrix. The mathematical technique used in PCA is called eigen analysis: one solves for the eigenvalues and eigenvectors of a square symmetric matrix with sums of squares and cross products. The eigenvector associated with the largest eigenvalue has the same direction as the first principal component. The eigenvector associated with the second largest eigenvalue determines the direction of the second principal component. The sum of the eigenvalues equals the trace of the square matrix and the maximum number of eigenvectors equals the number of rows (or columns) of this matrix.

Covariance information in some embodiments can be derived from calculating a dynamic cross-correlation map (DCCM). A DCCM is a map of cross-correlation coefficients for the displacement of any two atoms i and j and is given by:

$$C_{ij} = \langle \Delta r_i \cdot \Delta r_j \rangle / \sqrt{\langle \Delta r_i^2 \rangle \langle \Delta r_j^2 \rangle}$$

where $\Delta r_i$ is the displacement of atom i from its mean position. The map and the corresponding correlation coefficients can highlight regions of the protein that move in concert in a correlated manner vis-à-vis structural regions that are anticorrelated in their dynamics. Thus, in some embodiments, the covariance of residue displacements in the structure of a protein is used to identify hinge regions in the protein.

In some embodiments, the altered conformation is biased towards a principal low frequency mode of motion determined by an analysis selected from the group consisting of principal component analysis of molecular dynamics trajectory and anisotropic elastic network model analysis.

Step 404. In step 404, the three-dimensional coordinates of the polymer are altered by pivoting the first domain with respect to the second domain about the first hinge thereby obtaining an altered set of three-dimensional coordinates $\{x_{1A\_alt}, \ldots, x_{NA\_alt}, x_{1B\_alt}, \ldots, x_{MB\_alt}, x_{1C\_alt}, \ldots, x_{PC\_alt}, \ldots\}$ for the polymer, where atoms within the first domain are held fixed with respect to each other and atoms within the second domain are held fixed with respect to each other.

To appreciate step 404 it is instructive to point out that one or more hinge parameters are associated with any particular hinge. A hinge parameter refers to any quantity that can be used to describe or define a physical aspect of a hinge. For example, useful hinge parameters includes, without limitation, torsion angles, bond angles and interatomic distances. In some embodiments, the hinge parameter is a torsion angle. In exemplary embodiments, the hinge parameter is a torsion angle selected from the group consisting of $\phi$ and $\psi$ dihedral angles.

In some embodiments, the polymer comprises a plurality of hinges characterized by a plurality of hinge parameters. The plurality of hinge parameters may comprise only one type of hinge parameter or any combination of different hinge parameters.

Some embodiments of step 404 comprise applying an alteration to one or more hinge parameters of the first hinge in order to pivot one of the two domains connected to the first hinge with respect to the other of the two domains. In some embodiments, the alteration is applied to a subset of the hinge parameters of the first hinge. In some embodiments, the alteration is applied to a subset of a plurality of hinge parameters, where the subset is randomly chosen. In some embodiments, the alteration is random.

In some embodiments, an alteration to a hinge parameter that is applied in step 404 to achieve the pivot comprises a rotation about a single dihedral angle or concerted rotation about two or more dihedral angles at distant positions along the polymer sequence. In these embodiments, a hinged inter-domain movement or loop movement may be captured. In some embodiments, backrub moves (Davis et. Al. 2006) are employed to introduce the hinge alteration. See Davis, 2006, "The backrub motion: How protein backbone shrugs when a sidechain dances," Structure 14:265-274, which is hereby incorporated by reference herein in its entirety, for a description of this form of movement.

In some embodiments in which the polymer is a protein side chain geometries are packed in an alternate conformations once the hinge has been pivoted by applying a protein packing algorithm. A number of protein packing algorithms have been developed to search and optimize amino acid side chain geometries given a protein backbone geometry. See, for example, Jones, 1994, "De novo protein design using pairwise potentials and a genetic algorithm," Protein Sci 3 (4):567-74; Desmet et al., 1992, "The dead-end elimination theorem and its use in protein side-chain positioning," Nature 356 (6369):539-542; Holm and Sander, 1992, "Fast and simple Monte Carlo algorithm for side chain optimization in proteins: application to model building by homology," Proteins 14 (2):213-23; Lee and Subbiah, 1991, "Prediction of protein side-chain conformation by packing optimization," J Mol Biol 217 (2):373-88; and Kono and Doi, 1994, "Energy minimization method using automata network for sequence and side-chain conformation prediction from given backbone geometry," Proteins 19 (3):244-55, each of which is hereby incorporated herein in its entirety. Given a number of amino acid side chain geometries known as rotamers, these algorithms solve for the combination of optimal rotamer geometry for all the amino acids in the protein sequence. In some embodiments, the repacking step comprises optimizing side chain rotamer geometry for amino acids that are affected by the alteration as discussed herein.

In some embodiments of step 404 the first domain is pivoted with respect to the second domain by some amount without application of a change to a hinge parameter. In fact, in such embodiments, the residues of the first hinge are disregarded altogether. Once the pivot has been accomplished, the first hinge is rebuilt de novo based on the new locations of the first and second domain. Such rebuilding can be accomplished by implementation of the "loop closure problem." The loop closure problem has been applied, for example, in loop geometry prediction in homology models of proteins or by known methods of predicting the structure of missing loop sequences in protein structures. The loop closure problem in the context of protein structures is also known as inverse kinematics in the mathematical field. Given a polymer chain such that end points of the chain are constrained to specific locations, the problem deals with finding the right values for the underlying degrees of freedom, e.g., the backbone dihedral angles in the polymer chain. A number of analytical solutions to this problem are available. See, for example, Wedemeyer and Scheraga, 1999, "Exact analytical loop closure in proteins using polynomial equations," Journal of Computational Chemistry 20 (8):819-844; Coutsias et al., 2004, "A kinematic view of loop closure," J Comput Chem 25 (4):510-28, each of which is hereby incorporated by reference. In some embodiments, the methods comprise solving the loop closure problem associated with multiple distant torsion angle changes performed individually.

Step 406. In step 406 an energy value is calculated for the altered set of coordinates produced by the last instance of step 404.

The term "structural substate" describes a particular energy state. A folded polymer with a particular structure occupies a potential energy minimum. However, there are often more than one "local" minima of similarly low energy. When a polymer occupies any one of these minima, it has a distinct structure, or "substate". In addition to interconversion between substates, polymers undergo continuous structural fluctuations within a particular substate minimum. The scoring of step 406 helps to identify such substates.

In some embodiments, scoring the altered conformation comprises applying a performance metrics. Any of a number of performance metrics known in the art may be used. In some embodiments, the performance metric is a potential energy function. A potential energy function is a mathematical function that comprises terms accounting for bonds, angles, improper dihedrals, torsion and non-bonded interactions in a polymer. A potential energy function comprises any combination or subset of these terms, and may also include additional terms. Such an energy function can be referred to as a "physics-based energy function". In some embodiments the performance metric is a knowledge-based energy function, which is an alternate form of potential energy function in which the parameters are derived from a statistical analysis of residue or atomic pair frequencies observed in experimentally solved polymer three-dimensional structures. Thus, in some embodiments, the performance metric is selected from the group consisting of a physics-based energy function, a knowledge-based energy function and a combination thereof.

Non-bonded interactions refer to sections of the potential energy function that deal with through space interactions between atoms in the system that are not interacting via bonds, angles and dihedral terms. These include interactions with solvent and other environmental molecules. As an approximation, depending on the separation between the atoms they can be factored in or ignored in a given model. In some embodiments, the performance metric is a potential energy function comprising a valence term, a non-bonded interaction term, a solvation effect term or any combination thereof.

Step 408. In step 408, a determination is made as to whether the performance metric is deemed satisfied. If it is not (408-No), process control returns to step 404 where the coordinates of the polymer are again altered by pivoting. If it is (408-Yes), process control either passes to optional step 410 or the process ends.

In exemplary embodiments, loop 404-408 constitutes a Monte Carlo search on polymer conformation. Monte Carlo methods are a class of computational algorithms that rely on repeated random sampling to compute results. Such algorithms are useful in situations where it is impractical to compute an exact result with a deterministic algorithm. In some such embodiments the Monte Carlo simulation uses a Metropolis criterion. The Metropolis criterion in a Monte Carlo simulation introduces a temperature dependent energy function conditional that follows detailed balance to achieve equilibrium sampling of states. See Metropolis et al., 1953, "Equation of State Calculations by Fast Computing Machines," The Journal of Chemical Physics 21 (6):1087-1092, which is hereby incorporated by reference.

In traditional Monte Carlo approaches, perturbations are introduced anywhere along the primary sequence of the polymer and are restricted to very small magnitudes. In these traditional methods, making large moves leads to, in most cases, a disturbance of internal domain structures and unfavorable energetic states. Furthermore, in the case of polymers that are proteins, these perturbations are typically introduced in the 2(n−2) backbone dihedral angles, where n is the number of the plurality of amino acids of the protein. The present disclosure provides, in some embodiments, methods that utilize hinge parameter perturbations that are more likely to lead to energetically feasible states, and which will be accepted by the algorithm. In some embodiments, perturbations are restricted to a subset of dihedral angles in the hinge. In exemplary embodiments, fewer than 2(n−2) hinge parameters are altered, where n is the number of residues in the polymer. In these embodiments, the reduced number of perturbed hinge parameters advantageously results in an increase in speed and efficiency in performing the method. Thus, the disclosed methods overcome a major hurdle in the use of traditional Monte Carlo approaches for sampling polymer conformations.

In some embodiments, the methods comprise accepting or rejecting an altered conformation on the basis of a Metropolis criteria, as referenced above. In other words, respective instances of steps 404 and 406 are performed sequentially in time and an $n^{th}$ instance of step 404 alters the altered set of coordinates of the polymer produced by either the $n^{th}-1$ or the $n^{th}-2$ instance of the altering step 404, where this selection of the altered set of coordinates of the polymer for the $n^{th}$ instance of the altering step 404 is on the basis of the Metropolis criteria, and where n is a positive integer of three or greater. Thus, if the Metropolis criteria is not satisfied, the $n^{th}$ instance of the altering step 404 uses the coordinates for the $n^{th}-2$ instance of the altering step 404 and if the Metropolis criteria is satisfied, the $n^{th}$ instance of the altering step 404 uses the coordinates for the $n^{th}-1$ instance of the altering step 404.

In some embodiments, the hinge parameter is a backbone torsion angle and the altered conformation is biased towards stereochemically acceptable dihedral states. The art provides numerous ways of determining stereochemically acceptable dihedral states, for example, through Ramachandran maps (discussed above) and the like.

Step 410. Optionally, the altered set of coordinates serves as a starting point for an atomistic simulation. An atomistic simulation refers to a simulation protocol based on a model that describes a molecular system in terms of the individual atoms present in the system. Valence terms describing the bond topology connecting the atoms along with non-bonded pair-wise atomic interactions are employed to describe the system energy. See, Adcock McCammon, 2006, "Molecular dynamics: survey of methods for simulating the activity of proteins." Chem Rev 106 (5):1589-615, which is hereby incorporated by reference herein in its entirety. "Coarse grain models" simplify or abstract some of the aspects of molecular model to gain some advantage, for example, to reduce the need for computer resources.

Relative to coarse-grained modelling, fine-grained or atomistic modelling increases the level of detail in the molecular system being modelled. In some embodiments, an altered set of three-dimensional coordinates of the polymer is subjected to fine-grained, all-atom molecular dynamics simulations. In this way, a molecular dynamics simulation is more likely to lead to the sampling of unique conformational substates.

Thus, in exemplary embodiments, the methods comprise performing a molecular dynamics simulation of an altered conformation. Molecular dynamics (MD) is a form of computer simulation in which atoms and molecules are modeled in interaction over time using potential energy functions (as described above) approximating known physical properties. Molecular systems comprise a large number of particles, making it impossible to establish the nature of the systems analytically. MD simulation circumvents this problem by using numerical methods and allows researchers to characterize the dynamical properties of the system.

In a simplified description of the molecular dynamics simulation algorithm, simulation proceeds iteratively by alternatively calculating forces and solving the equations of motion based on the accelerations obtained from the new forces. In fact, without being bound by theory, most MD practices use much more complicated versions of the algorithm, including two steps in solving the equations of motion and many additional steps accounting for temperature and pressure control, analysis and output. Numerous methods of molecular dynamics simulation are known in the art and can be used to perform loop 404-408. Adcock and McCammon (2006) provide a general review of molecular dynamics methods useful in the present invention. See, Adcock McCammon, 2006, "Molecular dynamics: survey of methods for simulating the activity of proteins." Chem Rev 106 (5):1589-615, which is hereby incorporated by reference herein in its entirety.

In some embodiments, the molecular dynamics simulation comprises using an implicit or explicit solvent model. In contrast to explicit solvent models in which the solvent is treated at the atomic level, implicit solvent models represent the solvent as a continuum. See, for example, Lazaridis and Karplus, 1999, "Effective energy function for proteins in solution," Proteins: Structure, Function, and Genetics 35: 133-152, which is hereby incorporated herein by reference. In some embodiments, the methods comprise computing solvation energy of a system by an implicit solvent method.

In some embodiments, the molecular dynamics simulation comprises calculating a free energy landscape based on the altered conformation by using any of a number of suitable methods. In exemplary embodiments, a free energy landscape based on the altered conformation is calculated by a method selected from Umbrella Sampling, Thermodynamic Integration, Free Energy Perturbation, Adaptive Biasing Force based potential of mean force calculations and targeted molecular dynamics. Umbrella Sampling, Thermodynamic Integration, Free Energy Perturbation, or Adaptive Biasing Force based potential of mean force calculations are free energy simulation methods that employ a statistical mechanics based approach to derive the free energy difference between two states of a system.

In some embodiments, the methods comprise performing a Serial Replica Exchange (SRE) molecular dynamics simulation. Replica exchange refers to a molecular simulation algorithm in which a number of molecular dynamics simulations of the system of interest are performed at different temperatures synchronously. The Serial Replica Exchange method is an asynchronous method for running simulations of a system at different temperatures. See, for example, Hagen et al., 2007, "Serial replica exchange.", J Phys Chem B 111 (6):1416-23, which is hereby incorporated by reference herein in its entirety. In some embodiments, the SRE molecular dynamics simulation comprises temperature tempering or solvent tempering.

In some embodiments, the methods comprise generating a plurality of altered conformations. That is, certain of the sets of altered three-dimensional coordinates of the polymer from various instances of step 404 are saved. In some embodiments, each set of altered three-dimensional coordinate that satisfies some form of predetermined evaluation function is saved. In some embodiments, this evaluation function is the same as the performance metric only with less stringent criterion for satisfaction of the evaluation function. In some embodiments, the protonation state of an ionizable amino acid side chain varies among the plurality of altered conformations. In some embodiments, the methods comprise assigning each of the plurality of altered conformations to one of a plurality of conformational clusters, where the assigning step comprises using structural data selected from the group consisting of inter-domain geometric parameter, inter-atomic contact pattern, radius of gyration, solvent accessibility and root mean square deviation of the plurality of altered conformations. The process of separating a plurality of altered conformations into various subsets ("conformational clusters") is referred to as "clustering". The criterion for clustering is defined according to the needs of the practitioner. For example, the altered conformations of a conformational cluster may share values of a property selected from the group consisting of interdomain geometry, packing criteria such as contact order, accessibility of "hotspot" residues, and the like. The plurality of altered conformations of a conformational cluster may also be grouped according to structural data selected from the group consisting of inter-domain geometric parameter, inter-atomic contact pattern, radius of gyration, solvent accessibility and root mean square deviation of the plurality of altered conformations. The clustered conformations can be further analyzed by applying methods such as molecular dynamics.

In some embodiments, the methods comprise performing a plurality of independent molecular dynamics simulations. In some embodiments, the plurality of independent molecular dynamics simulations is performed in parallel (a) on nodes of a computer cluster, (b) in a distributed computing system or (c) by general purpose computing on graphics processing units. In some embodiments, if conformational similarity between intermediate structures in any two of the plurality of independent molecular dynamics simulations is within a certain threshold, one of the two molecular dynamics simulations is stopped. In some embodiments, the plurality of independent molecular dynamics simulations is performed on representative structures from conformational clusters described above.

In some embodiments, the molecular dynamics simulation comprises adaptively computing an energy distribution of a plurality of conformations.

Implementation in a computer system. The methods described may be implemented as computer programs that are executed on programmable computers comprising a processor and a data storage system. A computer program is a set of instructions that can be used, directly or indirectly, in a computer to perform a certain activity or to bring about a certain result. A computer program can be written in any form of programming language, including compiled or interpreted languages, and it can be deployed in any form, including as a stand-alone program or as a module, component, subroutine, function, procedure or other unit suitable for use in a computing environment.

The computer program can be stored in a non-transitory manner on a computer-readable storage system. Examples of storage systems include, without limitation, optical disks such as CD, DVD and Blu-ray Discs (BD); magneto-optical disks; magnetic media such as magnetic tape and internal hard disks and removable disks; semi-conductor memory devices such as EPROM, EEPROM and flash memory; and RAM. A computer-readable storage system may be physically transformed such that it contains a computer program. A computer-readable storage system comprising computer executable instructions is physically configured in such a manner so as to cause a computer interacting with the storage system to perform a process or a method.

Thus, in one aspect, the disclosure provides a computer-readable storage system comprising computer executable instructions for performing a method of altering an input conformation of a polymer to generate an altered conformation of the polymer in a computer system, where the polymer comprises (i) a plurality of residues and (ii) a hinge characterized by a hinge parameter, the method comprising (a) determining the location of the hinge; and (b) applying an alteration to the hinge parameter, thereby generating the altered conformation of the protein. In some embodiments, a computer-readable storage medium comprises computer executable instructions that cause a computer to perform any of the methods disclosed herein.

In a further aspect, a computer system is disclosed for performing a method of altering an input conformation of a polymer to generate an altered conformation of the polymer, where the polymer comprises (i) a plurality of residues and (ii) a hinge characterized by a hinge parameter, the system comprising a data storage system and a processor comprising instructions for performing a method comprising (a) determining the location of the hinge; and (b) applying an alteration to the hinge parameter. In some embodiments, a computer system for performing a method of altering an input conformation of a polymer to generate an altered conformation of the polymer, where the polymer comprises (i) a plurality of residues and (ii) a hinge characterized by a hinge parameter, comprises a data storage system and a processor comprising instructions for performing any of the methods disclosed herein.

The processor and the data storage system can be supplemented by or incorporated in application-specific integrated circuits (ASICs). When read into the processor of the computer, which is thus physically transformed, and executed or further processed before execution, the instructions of the program cause the programmable computer to carry out the various operations described above. The processor and the data storage system are typically connected by a bus.

To provide for interaction with a user, the invention can be implemented on a computer having a display device such as, for example, a cathode ray tube (CRT) or liquid crystal display (LCD) monitor for displaying information to the user. The user can provide input, for example, via a keyboard and a pointing device such as a mouse. The various conformations generated by the present methods can be represented graphically using molecular modeling and graphics software.

The different aspects and embodiments of the invention can be implemented in a computer system that includes a backend component such as a data server, a middleware component such as an application server or an Internet server, or a frontend component such as a client computer having a user interface, Internet browser or any combination thereof. The components of the system can be connected by any form or medium of digital data communication.

The present methods can be implemented on hardware in a variety of configurations. Thus, in some embodiments, computational processes (such as, for example, a plurality of molecular dynamics simulations) are performed in parallel on nodes of a computer cluster, in a distributed computing system or on graphics processing units as these configurations are understood in the art.

Applications

Polymers commonly undergo large-scale conformational change in a wide range of functionally critical activities. The disclosed methods fill an important gap in better understanding polymer conformational sub-states and the energetic factors determining transitions between them. This in turn enables the design of optimized polymers for a variety of uses.

In one embodiment, the combined Monte Carlo/Molecular Dynamics simulation method described here is used to model, verify and explain the various conformational states and data observed in FRET (fluorescence resonance energy transfer) experiments or other low-resolution structural methods like cryo-electron microscopy.

In a structure guided molecular design approach, be it in the context of drug design or protein engineering, it is desirable to characterize the dynamic nature of proteins and their alternate conformational states. For example, the functionally relevant geometry of a polymer when it binds its target could be different from its geometry in the unbound state. The design of a drug or polymer can be optimized on the basis of these alternate conformational states. In one aspect, the present disclosure provides a method to describe the alternate conformation states of a polymer.

Figure 7:
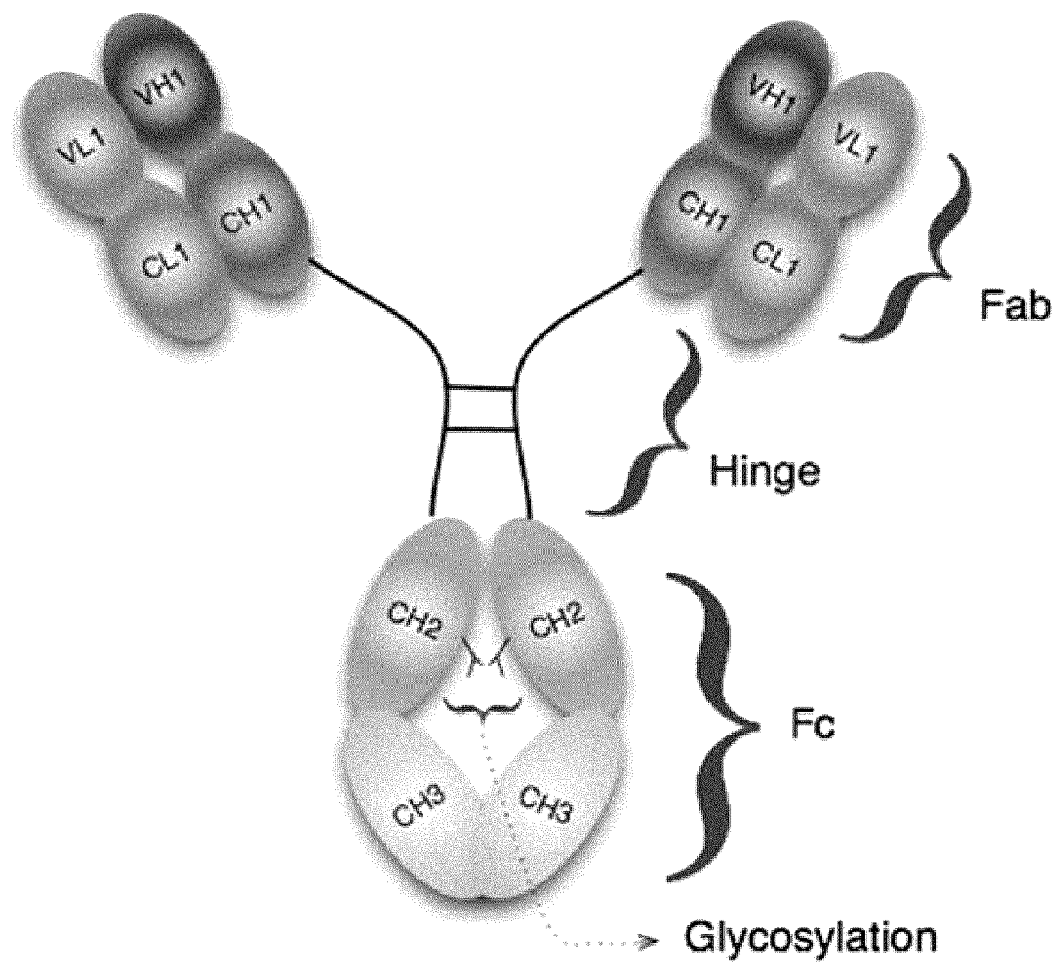
FIG. 7 shows a schematic representation of an antibody IgG molecule. It is a homodimeric structure held together by disulphide links and non-covalent interactions between various domains. The hinge connects the Fab region to the Fc portion of the IgG molecule. The hinge is 15 amino acids long in the case of IgG1, 12 amino acids long in IgG2 and IgG4 and 64 amino acids long in IgG3.

In one embodiment, the method can be used in the design and optimization of protein based therapeutics with two or more valencies, where the term valency as used here refers to the antigen or target-binding component of the therapeutic. These multivalent therapeutic molecules capable of binding multiple antigens may be sterically and structurally hindered from binding all its targets with all its valencies. In one embodiment, if the interest is to optimize or evaluate the binding ability of an antibody (e.g., shown schematically in FIG. 7) to its target antigen and co-engage e.g. concurrently bind target antigens with both arms, the systems and methods described in this disclosure can be employed. One would first model the geometry of the two targets relative to each other. Next one can employ the method described here to evaluate if the candidate molecule with the available hinge configuration is capable of co-engaging both the target antigens. In an alternate embodiment, one may employ the disclosed systems and methods to determine the optimal hinge composition that can achieve the co-engagement. Such an approach can also be employed in the design and development of bispecific and other multispecific, multivalent or multifunctional molecules that can engage more than one molecule concurrently. In some embodiments, the systems and methods are employed to evaluate and model the docking of a therapeutic molecule to the target receptors.

In one aspect, the present disclosure provides a method of producing a polymer in which the polymer is first designed and then made. In exemplary embodiments, the polymer is a polymer variant characterized by an improved polymer property compared to a reference polymer. The term "polymer properties" refers to physical, chemical and biological characteristics including but not limited to physical properties (including molecular weight, hydrodynamic properties such as radius of gyration, net charge, isoelectric point, and spectral properties such as extinction coefficient), structural properties (including secondary, tertiary, and quaternary structural elements) stability (including thermal stability, stability as a function of pH or solution conditions, storage stability, and resistance or susceptibility to ubiquitination, proteolytic degradation, or chemical modifications such as methionine oxidation, asparagine and glutamine deamidation, sidechain racemerization or epimerization, and hydrolysis of peptide bonds), solubility (including susceptibility to aggregation under various conditions, oligomerization state, and crystallizability), kinetic and dynamic properties (including flexibility, rigidity, folding rate, folding mechanism, allostery, and the ability to undergo conformational changes and correlated motions), binding affinity and specificity (to one or more molecules including proteins, nucleic acids, polysaccharides, lipids, and small molecules, and including affinities and association and dissociation rates), enzymatic activity (including substrate specificity; association, reaction and dissociation rates; reaction mechanism; and pH profile), amenability to chemical modification or derivitization (including PEGylation and attachment to other molecules or surfaces), expression properties (such as yield in one or more expression hosts, soluble versus inclusion body expression, subcellular localization, ability to be secreted, and ability to be displayed on the surface of a cell), processing and posttranslational modifications (including proteolytic processing, N- or C-linked glycosylation, lipidation, sulfation, and phosphorylation), pharmacokinetic and pharmacodynamic properties (including bioavailability following subcutaneous, intramuscular, oral, or pulmonary delivery; serum half-life, distribution, and mechanism and rate of elimination) and ability to induce altered phenotype or changed physiology (including immunogenicity, toxicity, ability to signal or inhibit signaling, ability to stimulate or inhibit cell proliferation, differentiation, or migration, ability to induce apoptosis, and ability to treat disease).

Once designed, polymers may be easily manufactured by known methods. For example, in the case where the polymer is a protein, methods of protein expression using exogenous nucleic acid in host cells can be sued. Such approaches are well known in the art and the specific implementation details will vary with the host cell used. The exogenous nucleic acid, which encodes the protein of interest, can be made by total gene synthesis or by site-directed mutagenesis of a nucleic acid encoding wild type or variant protein. Methods including template-directed ligation, recursive PCR, cassette mutagenesis, site-directed mutagenesis or other techniques that are well known in the art may be utilized.

The exogenous nucleic acid can be part of a larger construct such as an expression vector. Numerous types of appropriate expression vectors comprising the exogenous nucleic acid and suitable regulatory sequences for a variety of host cells are known in the art. The expression vectors may contain transcriptional and translational regulatory sequences selected from promoter sequences, ribosomal binding sites, transcriptional start and stop sequences, translational start and stop sequences, transcription terminator signals, polyadenylation signals, enhancer or activator sequences, selectable marker genes to allow the selection of transformed host cells, and the like.

Expression vectors and exogenous nucleic acid encoding the protein of interest may be introduced into a host cell by techniques including dextran-mediated transfection, calcium phosphate precipitation, calcium chloride treatment, polybrene mediated transfection, protoplast fusion, electroporation, viral or phage infection, encapsulation of the polynucleotide(s) in liposomes, direct microinjection of the DNA into nuclei and the like. The exogenous nucleic acids may stably integrate into the genome of the host cell or may exist either transiently or stably in the cytoplasm.

Following production, polymers may be isolated or purified in a variety of ways known to those skilled in the art. Standard purification methods include chromatographic techniques, including ion exchange, hydrophobic interaction, affinity, sizing or gel filtration, and reversed-phase, carried out at atmospheric pressure or at high pressure using systems such as FPLC and HPLC. Purification methods also include electrophoretic, immunological, precipitation, dialysis, and chromatofocusing techniques. Ultrafiltration and diafiltration techniques, in conjunction with protein concentrating methods, are also useful. For general guidance in suitable purification techniques, see Scopes, *Protein Purification: Principles and Practice* (3rd ed., 1994), which is hereby incorporated herein in its entirety.

The functional and biophysical properties of the polymers of the present invention can be screened in various assays, particularly using in vitro methods. In vitro assays may allow a broad dynamic range for screening protein properties of interest. Multiple properties may be screened simultaneously or individually. The molecules may be purified or unpurified, depending on the requirements of the assay. Binding assays can be carried out using a variety of methods known in the art, including but not limited to FRET (Fluorescence Resonance Energy Transfer) and BRET (Bioluminescence Resonance Energy Transfer)-based assays, AlphaScreen™ (Amplified Luminescent Proximity Homogeneous Assay), Scintillation Proximity Assay, ELISA (Enzyme-Linked Immunosorbent Assay), SPR (Surface Plasmon Resonance, also known as BIACORE®), isothermal titration calorimetry, differential scanning calorimetry, gel electrophoresis, chromatography including gel filtration and the like. Assays may employ a variety of detection methods using, for example, chromogenic, fluorescent, luminescent, or isotopic labels.

Accordingly, the present disclosure provides compositions comprising a polymer variant characterized by an improved physical property compared to a reference polymer. The polymer variant can be designed and made using any of the methods described herein. The compositions of the invention can be administered to a patient to treat a disorder. Administration of the compositions can occur through various routes including topical, enteral and parenteral routes.

The present disclosure also provides pharmaceutical compositions comprising a polymer variant of the invention and a carrier. Suitable carriers include fillers such as microcrystalline cellulose, lactose, corn and other starches; binding agents; sweeteners and other flavoring agents; coloring agents; polyethylene glycol and the like. The *Encyclopedia of Pharmaceutical Technology* (James Swarbrick, ed., 3d ed. 2007), which is hereby incorporated herein in its entirety, provides a broad range of techniques useful for formulating the proteins of the present invention.

The articles "a," "an" and "the" as used herein do not exclude a plural number of the referent, unless context clearly dictates otherwise. The conjunction "or" is not mutually exclusive, unless context clearly dictates otherwise. The term "include" is used to refer to non-exhaustive examples.

EXAMPLE 1

A prototype that samples defined protein hinge regions using basic torsional angle Monte Carlo moves has been created. The moves are defined as torsional angle moves on the sidechains as well as the backbone. The purpose of this method is to sample the space available to large protein domains that are connected with a hinge to another part of the system that remains fixed, as well as estimate the conformational space available to branched carbohydrates in a system.

Figure 8:
FIG. 8 shows two scFv's fused to albucore using two linkers in accordance of an exemplary embodiment of the present disclosure. The linker functions as a hing between albacore and the two scFv's.

In this example, as illustrated in FIG. 8, an Albumin based molecule (Albucore) is fused to two scFvs attached to each terminal of the Albumin. The linkers are A/334-A/350 as well as B/255-B/270 and function as a hinge in this molecule. The moving regions are A/351 and above as well as B/254 and below. Reasonable side-chains to move are: A/352, A/378, A/547, A/547, A/450, A/293, A/290, A/294, A/333, A/297, B/314, B/371, B/307, B/311, B/225, B/224, B/150, B/149. Since the goal of the method is to estimate an upper bound on the volume (conformational space) sampled by the two mobile scFvs linked by the hinge to albumin, a temperature increase or a coarse-grained potential could also be employed to improve the sampling efficiency of the algorithm.

Using the AMBER potential and at temperature of 10,000K, five Monte Carlo simulations were run that sampled the two scFv domains for 25,000 steps starting from the same initial condition (but with different random seeds). The ratios for the moves was set to 75% backbone torsion sampling and 25% sidechain torsion sampling. In order to characterize the trajectories and the orientation and geometry of the two scFv's relative to each other and the fixed Albumin domains, the following metrics were calculated for each one:

One. The distance between residue B/232 and A/395 was sampled (by selecting an atom in each of these residues to calculate the distance).

Two. The distance between residue B/232 and the base of the hinge, residue B/271.

Three. The distance between residue A/395 and the base of the hinge, residue A/333.

Four. Using the base of the hinge for each domain as the origin of a spherical coordinate system, the polar and azimuthal angles of the location of the two domains along the trajectory was calculated.

Five. Using zapp close residue, the contacts between the moving domains and the fixed domain of Albucore was estimated. A plot showing the number of frames where each residue of the fixed domain is in contact with the mobile domains was made.

Six. To get a sense of the quality of the backbone hinge conformations, zapp backbone_strain was used to check how often the backbone conformations in the region have been strained.

Seven. The residues comprising the hinge were mutated to different residue compositions to determined impact on flexibility. As a test mutation of all hinge residues to proline resulted in a less flexible hinge than the original one, and this change was reflected in the sampling. In alternate experiments, all the residues of the hinge were mutated to alanine to increase flexibility characteristics of the hinge.

While AMBER is a physics based energy function comprising ab-inito quantum calculation derived charge value and other empirically derived parameters, simpler simulations could be performed using a more empirical protein residue/atom crystal structure derived statistical potentials, also known as knowledge based potentials.

FIG. 18 is an example of a script for zapp hinge sampling in accordance with this example.

Figure 9:
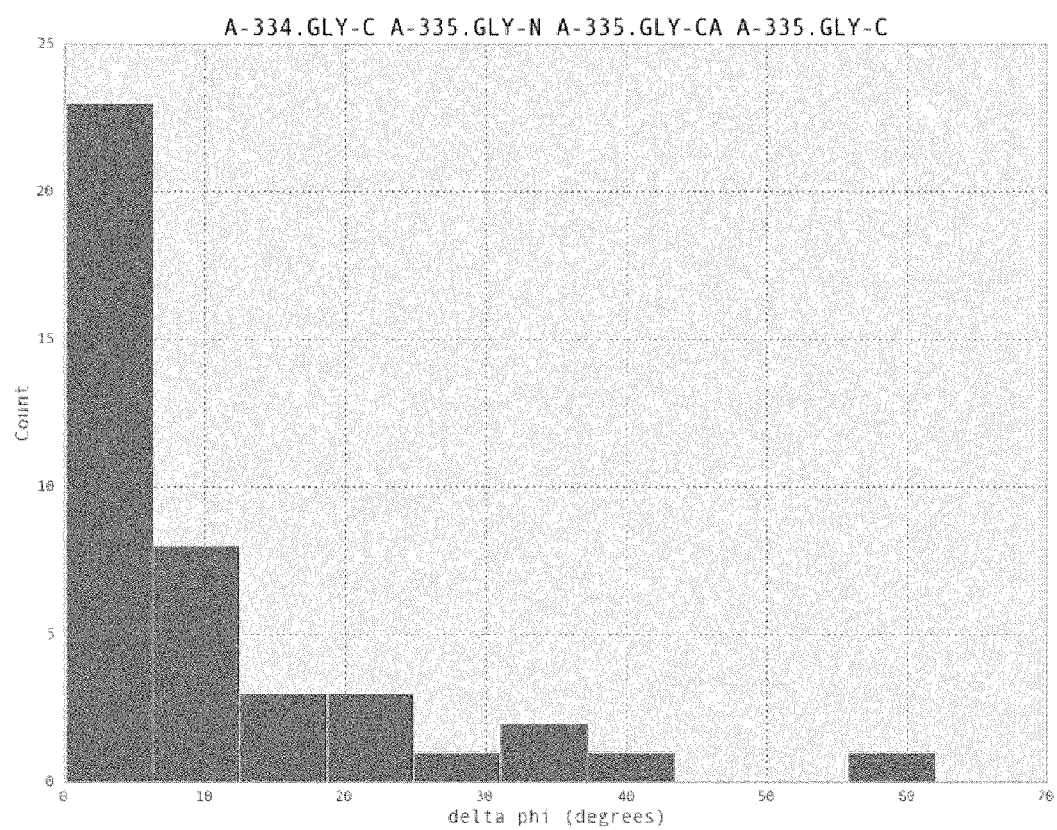
FIG. 9 shows a histogram distribution of accepted angles for three categories of hinge residues: base of the hinge, middle of the hinge and one closest to the moving domain. The phi and psi angles are plotted separately. The accepted angles for the torsions closest to the base of the hinge are significantly smaller than those accepted nearest to the moving region. This is rationalized on the basis that moves in torsion angles nearest to the base of the hinge will result in much larger fixed body rotations.

FIG. 9 shows the distribution of accepted angles for three categories of hinge residues in this example: base of the hinge, middle of the hinge and one closest to the moving domain. The phi and psi angles are plotted separately. The accepted angles for the torsions closest to the base of the hinge are significantly smaller than those accepted nearest to the moving region. This is rationalized on the basis that torsion angles nearest to the base of the hinge will result in much larger fixed body rotations.

Figure 10:
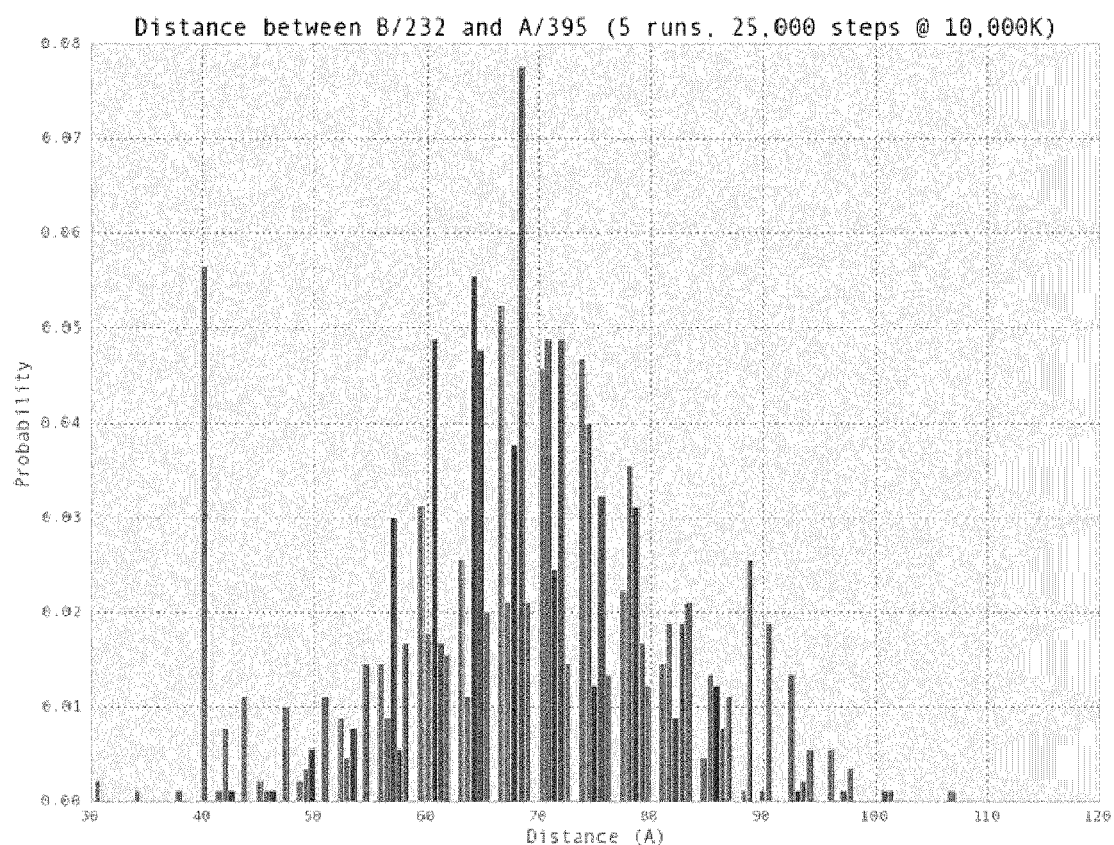
FIG. 10 shows the probability of distance between B/232 and A/395 in wild type Albumin based protein molecule in accordance with an example of the present disclosure.

In this example, sampling convergence of the above-described Albucore system was characterized with the following AMBER acceptance ratios: total 0.244, sidechain 0.747, linker 0.076, DDRW acceptance ratios: total 0.213, sidechain 0.849, linker 0.006 (for one run of 10,000 steps, 10,000K). FIG. 10 illustrates the distance between B/232 and A/395 in the Monte Carlo simulation (5 runs, 25,000 steps at 10,000K).

Figure 11:
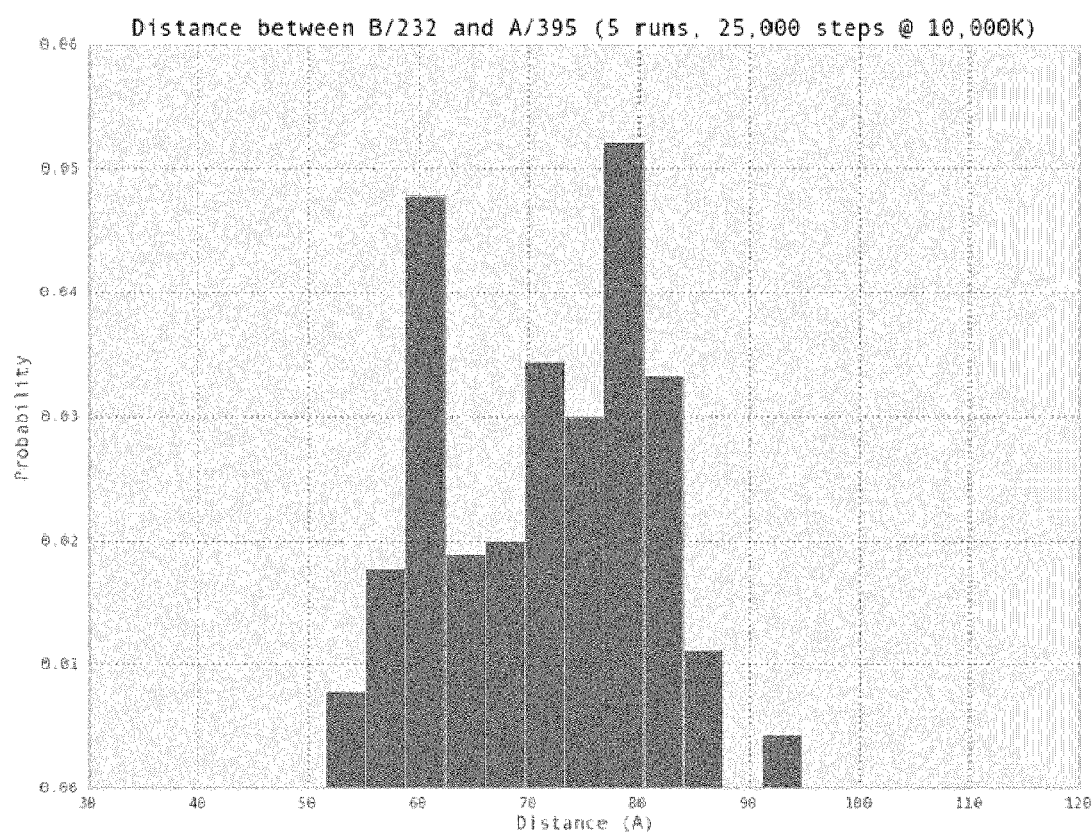
FIG. 11 shows a histogram distribution of the distance between B/232 and A/395 using the same structure used to for FIG. 10 with the exception that hinge residues have been mutated to proline.

Mutating the hinge residues to proline. The hinge resides in both chains were mutated to proline using a mutations application programming interface. When the sampling was performed on the resulting structure, the acceptance ratios for this sampling run were significantly lower for the hinge region (acceptance ration: total 0.215, sidechain 0.742, linker 0.038). Note this is roughly half the acceptance ratio for the hinge compared to the wildtype structure implying that the hinge is less flexible. FIG. 11 illustrates the distance between B/232 and A/395 in the Monte Carlo simulation (5 runs, 25,000 steps at 10,000K) when the hinge residues are mutated to proline.

Figure 12:
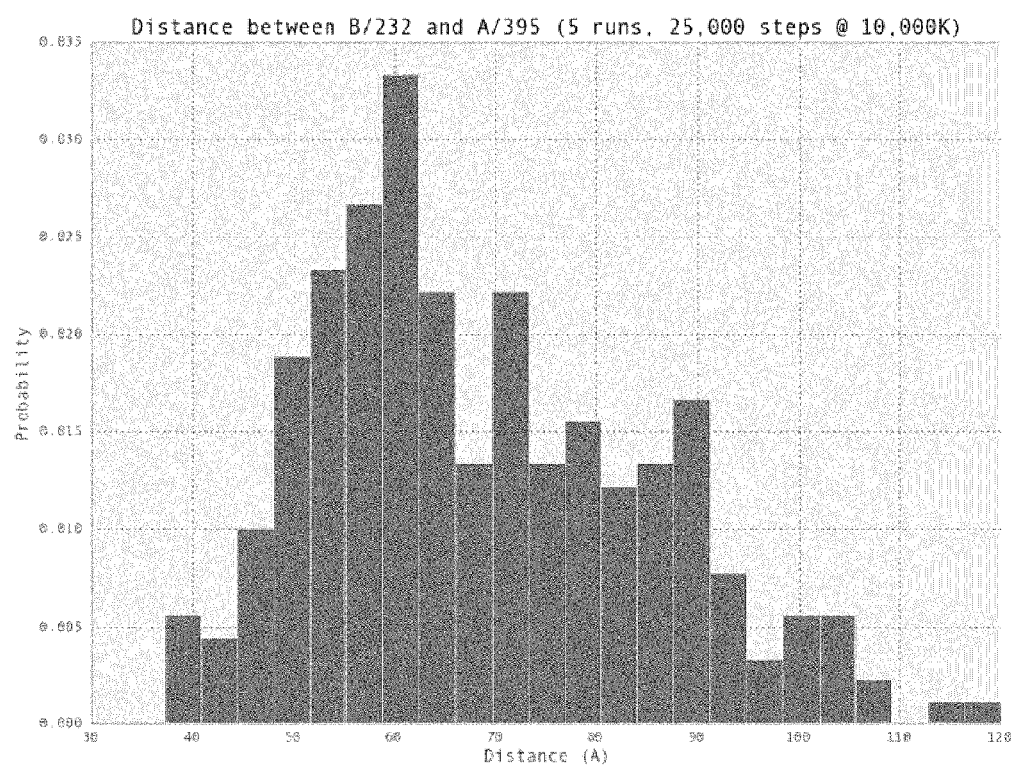
FIG. 12 shows a histogram distribution of the distance between B/232 and A/395 using the same structure used to for FIG. 10 with the exception that all residues other than hinge residues have been mutated to alanine.

Mutating all but hinge residues to alanine. On the other hand, mutation of hinge residues to alanine significantly increased the conformational accessibility as a result of the hinge motion, as illustrated in FIG. 12.

Summary of Observations for the Albucore system. The distance distributions for the five sampling runs above demonstrate that the moving regions are able to access the same volumes and do not get trapped given different random seeds. When all residues except for the hinge region are mutated to alanine, the moving region appears to be able to access a larger volume, although this could simply be due to higher number of accepted moves. Conversely, when the hinge residues were mutated to proline, the acceptance ratio dropped by a factor of two, implying that the hinge is less flexible than wild-type under these conditions.

Figure 13:
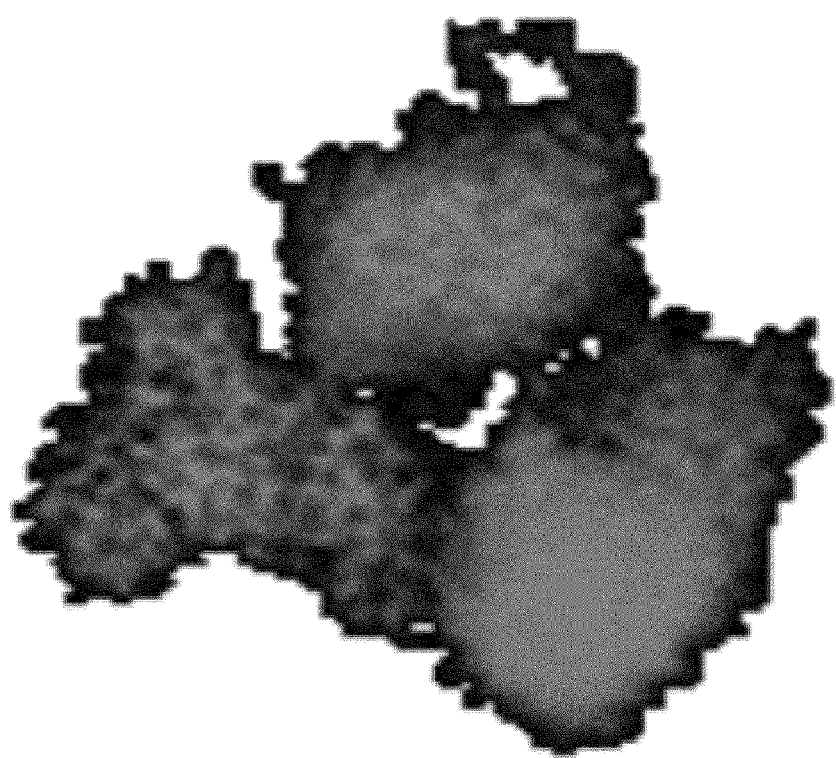
FIG. 13 provides a screenshot of an alternative structure in accordance with some embodiments.
Figure 14:
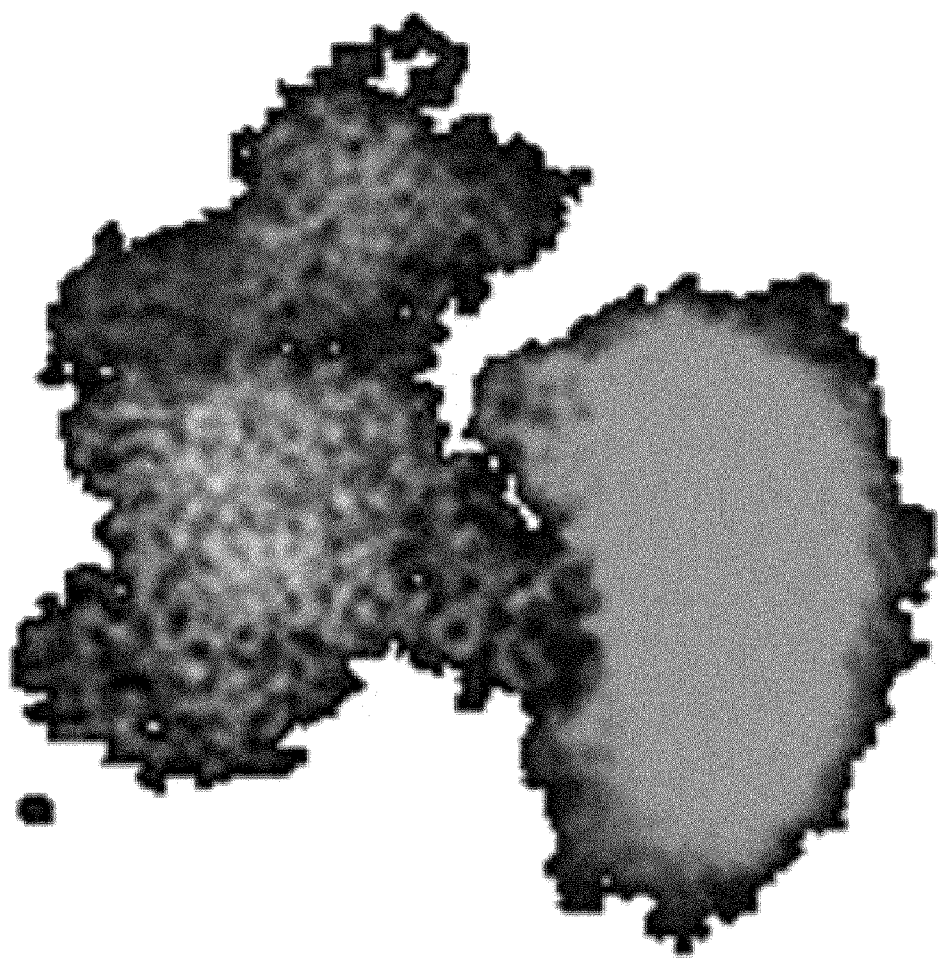
FIG. 14 provides a screenshot of an alternative structure in accordance with some embodiments.

FIGS. 13 and 14 provide screenshots of alternate structures representing conformations of the mobile domain.

EXAMPLE 2

Figure 15:
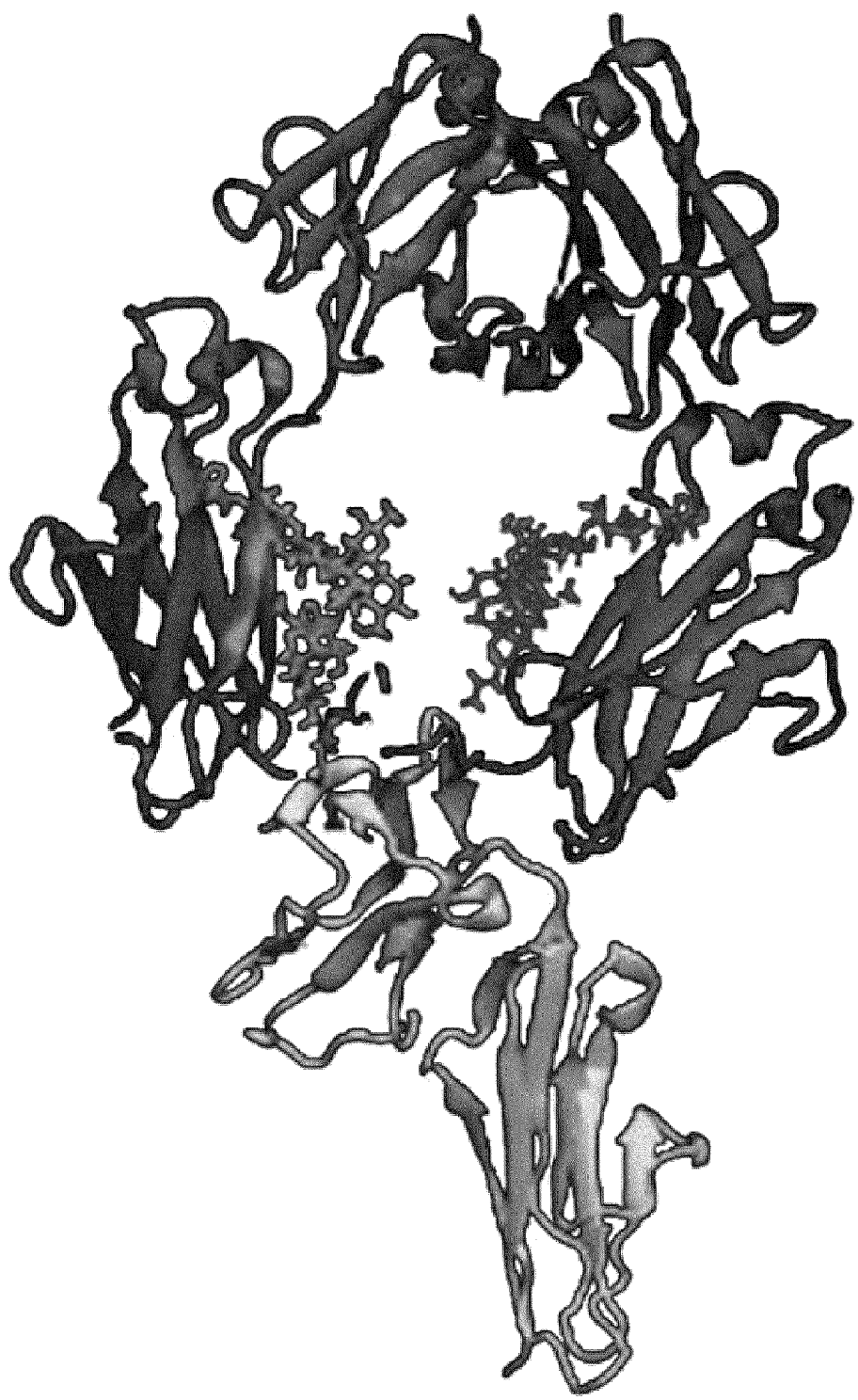
FIG. 15 provides an illustration of an Fc complex in accordance with some embodiments.
Figure 16:
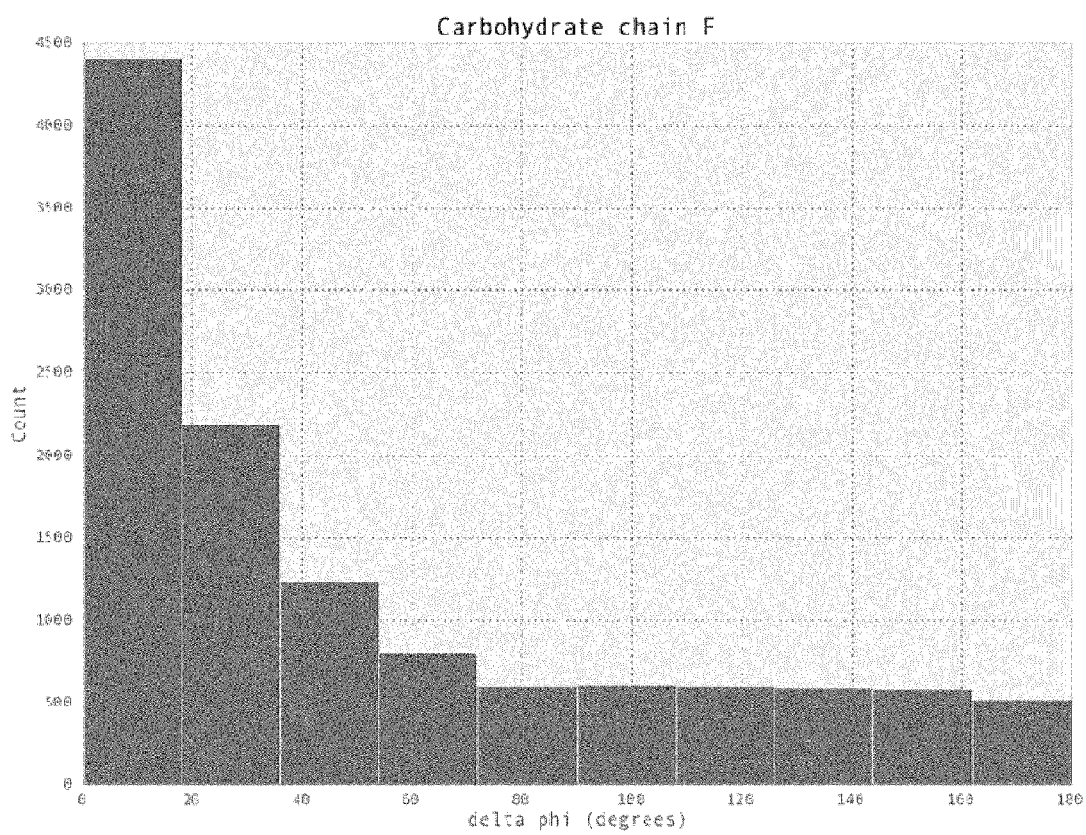
FIG. 16 provides a histogram for one carbohydrate chain in the Fc structure of FIG. 15.
Figure 17:
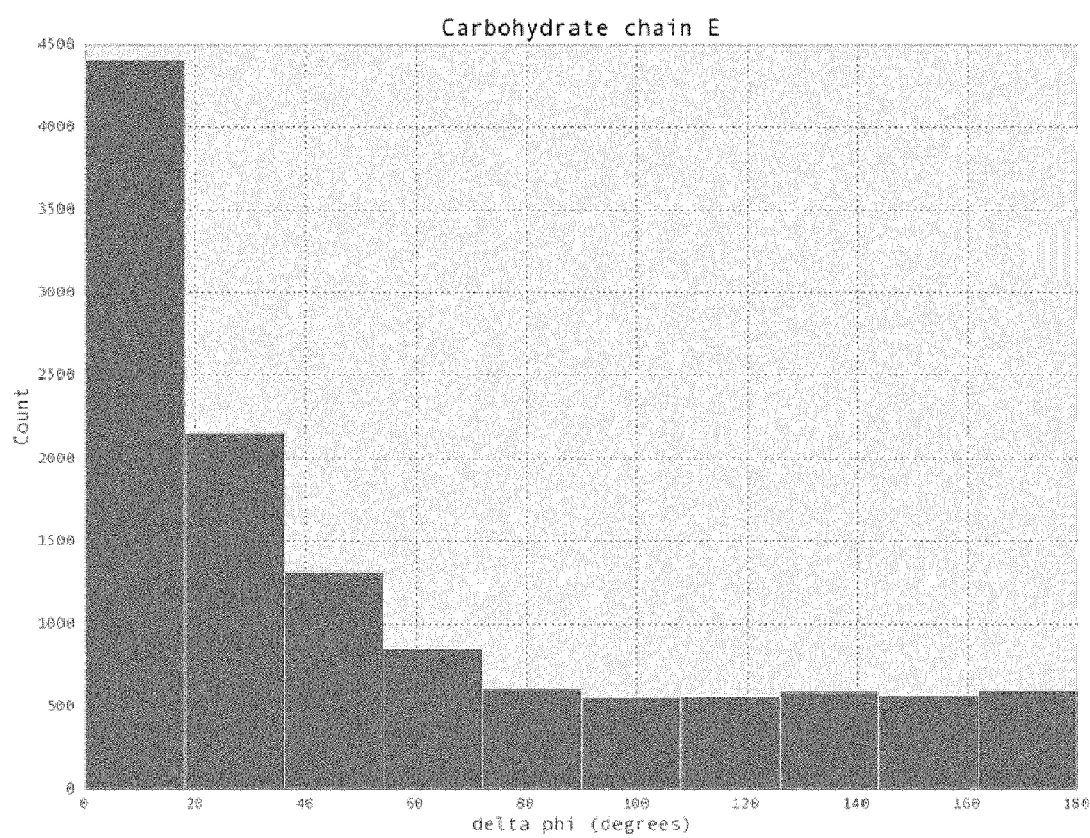
FIG. 17 provides a histogram for another carbohydrate chain in the Fc structure of FIG. 15.

A prototype that samples defined protein hinge regions using basic torsional angle Monte Carlo moves has been created. In this example, carbohydrate sampling is performed. The moves are defined as torsional angle moves on the glycosidic bond in the carbohydrate. The purpose of this application is to sample the conformational space available to branched carbohydrate groups employing the glycosidic bond as a hinge connecting the sugars and the protein. The carbohydrate sampling was tested on the Fc antibody region in complex with the FcRIIIa Receptor. There are two carbohydrate molecules in the system (chain E, F) attached to the Fc portion of the antibody at residues position 297 in the antibody chain at an Asn residue. FIG. 15 provides an illustration of the Fc complex with the carbohydrate chains E and F. The two carbohydrate chains were sampled at 1000K, 2000K for over 1,000,000 Monte Carlo steps and the characteristics illustrated in FIG. 19 were evaluated to establish its conformational freedom. FIGS. 17 and 18 are respectively two histograms for each carbohydrate chain in the Fc structure.

Based on this run, the following observations were made. The residue contacts convergence graphs show that the trajectories compared show a very good overlap in terms of which residues are in contact for both the Albucore simulations as well as the carbohydrate sampling. There seem to be some exceptions where certain residues were in contact in one trajectory more often than in another but in general their number is small and the frequency of the contact in the trajectory is not so high. The figures that track the accepted moves of certain residues in terms of phi, psi angles versus the backbone stress results inform us that: (i) for the wild type hinge and the residues shown the phi-psi angles change quite frequently while sampling bad conformations more often than when they sample good (there is no issue of something simply transitioning to a bad conformation and not moving at all), and (ii) for the proline hinge and the residues shown the conformations are strained throughout the trajectory, starting from bad conformations (the fact that the phi value remains constant has to do with the fact that this angle involves a closed loop and is therefore excluded by TAS, so the minor differences shown in the figures are numerical).

CONCLUSION

All references, publications, patent applications, issued patents, accession records and databases cited herein, including in any appendices, are incorporated by reference in their entirety for all purposes.

I claim:

1. A method of sampling and analysis of protein conformational dynamics by searching the conformation space of a protein to determine whether a three-dimensional conformation of the protein can co-engage each antigen in a plurality of target antigens, the protein comprising a first plurality of residues, the method comprising:
at a computer system having one or more processors and memory storing one or more programs to be executed by the one or more processors:
(A) obtaining from the memory an initial set of three-dimensional coordinates $\{x_{1A\_init}, \ldots, x_{NA\_init}, x_{1B\_init}, \ldots, x_{MB\_init}, x_{1C\_init}, \ldots, x_{PC\_init}, \ldots\}$ for the protein, wherein
the polymer comprises a plurality of domains,
each respective $x_{iA}$ in $\{x_{1A\_init}, \ldots, x_{NA\_init}, x_{1B\_init}, \ldots, x_{MB\_init}, x_{1C\_init}, \ldots, x_{PC\_init}, \ldots\}$ is a three dimensional coordinate for an atom in a first domain in the plurality of domains,
each respective $x_{iB}$ in $\{x_{1A\_init}, \ldots, x_{NA\_init}, x_{1B\_init}, \ldots, x_{MB\_init}, x_{1C\_init}, \ldots, x_{PC\_init}, \ldots\}$ is a three dimensional coordinate for an atom in a second domain in the plurality of domains, and
each respective $x_{iC}$ in $\{x_{1A\_init}, \ldots, x_{NA\_init}, x_{1B\_init}, \ldots, x_{MB\_init}, x_{1C\_init}, \ldots, x_{PC\_init}, \ldots\}$ is a three dimensional coordinate for an atom in a first hinge of the protein, wherein the first hinge comprises a second plurality of residues that is a subset of the first plurality of residues, wherein the protein is characterized by an ability for the first and second domain to pivot with respect to each other about the first hinge;
(B) altering the initial set of three-dimensional coordinates of the protein by pivoting the first domain with respect to the second domain about the first hinge thereby obtaining an altered set of three-dimensional coordinates $\{x_{1A\_alt}, \ldots, x_{NA\_alt}, x_{1B\_alt}, \ldots, x_{MB\_alt}, x_{1C\_alt}, \ldots, x_{PC\_alt}, \ldots\}$ for the protein, wherein
all atoms within the first domain are held fixed with respect to each other during the altering, and
all atoms within the second domain are held fixed with respect to each other during the altering;
(C) scoring, using a scoring module, a calculated potential energy of the altered set of coordinates versus a calculated potential energy of the initial three-dimensional coordinates for the protein with a Metropolis criterion, wherein, when the Metropolis criterion is satisfied, the altered set of three-dimensional coordinates is accepted as the initial set of three-dimensional coordinates;
(D) performing additional instances of the altering (B) and the scoring (C) until an energy of the altered set of three-dimensional coordinates $\{x_{1A\_alt}, \ldots, x_{NA\_alt}, x_{1B\_alt}, \ldots, x_{MB\_alt}, x_{1C\_alt}, \ldots, x_{PC\_alt}, \ldots\}$ satisfy the Metropolis criterion; and
(E) evaluating whether the altered set of three-dimensional coordinates $\{x_{1A\_alt}, \ldots, x_{NA\_alt}, x_{1B\_alt}, \ldots, x_{MB\_alt}, x_{1C\_alt}, \ldots, x_{PC\_alt}, \ldots\}$ can co-engage each antigen in the plurality of target antigens by docking the altered set three-dimensional coordinates to a model of the plurality of antigens.

2. The method of claim 1, the method further comprising, prior to the altering (B):
determining the residues of the hinge on the basis of solvent accessibility and contacts made by the second plurality of residues in the initial set of three-dimensional coordinates.

3. The method of claim 1, wherein the protein comprises a plurality of hinges, the plurality of hinges including the first hinge, wherein, for each respective hinge in the plurality of hinges, there is a corresponding pair of domains in the plurality of domains that pivot with respect to each other about the respective hinge, the method further comprising, prior to the altering (B):

determining the identity of the residues in each hinge in the plurality of hinges on the basis of solvent accessibility and contacts made by the second plurality of residues in the initial set of three-dimensional coordinates.

4. The method of claim 3, wherein the altering further pivots a third domain with respect to a fourth domain in the plurality of domains about a second hinge in the plurality of hinges, wherein all atoms within the third domain are held fixed with respect to each other during the pivoting of the third domain with respect to the fourth domain, and all atoms within the fourth domain are held fixed with respect to each other during the pivoting of the third domain with respect to the fourth domain.

5. The method of claim 1, wherein the scoring (C) comprises solving a loop closure problem for the first hinge to concurrently introduce alterations to some or all of a plurality of hinge parameters associated with the first hinge.

6. The method of claim 1, wherein the first hinge comprises a plurality of hinge parameters and wherein fewer than $2(n-2)$ hinge parameters are altered in the pivoting of the first domain with respect to the second domain about the first hinge, wherein n is the number of residues in the second plurality of residues.

7. The method of claim 1, the method further comprising, prior to the altering (B), determining the location of the first hinge by subjecting the initial set of three-dimensional coordinates to normal mode analysis.

8. The method of claim 1, wherein the protein comprises a plurality of hinges, the plurality of hinges including the first hinge, wherein, for each respective hinge in the plurality of hinges, there is a corresponding pair of domains in the plurality of domains that pivot with respect to each other about the respective hinge, the method further comprising, prior to the altering (B), determining the identity of the residues in each hinge in the plurality of hinges by subjecting the initial set of three-dimensional coordinates to normal mode analysis.

9. The method of claim 1, the method further comprising, prior to the altering (B), determining the residues of the polymer that comprise the first domain, the first hinge, and the second domain by principal component analysis.

10. The method of claim 1, wherein the protein comprises a plurality of hinges, the plurality of hinges including the first hinge, wherein, for each respective hinge in the plurality of hinges, there is a corresponding pair of domains in the plurality of domains that pivot with respect to each other about the respective hinge, the method further comprising, prior to the altering (B), determining the identity of the residues in each hinge in the plurality of hinges is performed by principal component analysis.

11. The method of claim 1, the method further comprising, prior to the altering (B), determining the residues of the protein that comprise the first domain, the first hinge, and the second domain by subjecting the initial set of three-dimensional coordinates to covariance analysis.

12. The method of claim 1, wherein the protein comprises a plurality of hinges, the plurality of hinges including the first hinge, wherein, for each respective hinge in the plurality of hinges, there is a corresponding pair of domains in the plurality of domains that pivot with respect to each other about the respective hinge, the method further comprising, prior to the altering (B), determining the identity of the residues in each hinge in the plurality of hinges by subjecting the initial set of three-dimensional coordinates to covariance analysis.

13. The method of claim 1, the method further comprising, prior to the altering (B): determining the residues of the protein that comprise the first domain, the first hinge, and the second domain by subjecting the initial set of three-dimensional coordinates to protein domain analysis.

14. The method of claim 1, wherein the protein comprises a plurality of hinges, the plurality of hinges including the first hinge, wherein, for each respective hinge in the plurality of hinges, there is a corresponding pair of domains in the plurality of domains that pivot with respect to each other about the respective hinge, the method further comprising, prior to the altering (B), determining the identity of the residues in each hinge in the plurality of hinges by subjecting the initial set of three-dimensional coordinates to protein domain analysis.

15. The method of claim 1, the method further comprising, prior to the altering (B), determining the determining the residues of the polymer that comprise the first domain, the first hinge, and the second domain comprises subjecting the initial set of three-dimensional coordinates to rigidity analysis.

16. The method of claim 1, wherein the protein comprises a plurality of hinges, the plurality of hinges including the first hinge, wherein, for each respective hinge in the plurality of hinges, there is a corresponding pair of domains in the plurality of domains that pivot with respect to each other about the respective hinge, the method further comprising, prior to the altering (B), determining the identity of the residues in each hinge in the plurality of hinges comprises subjecting the initial set of three-dimensional coordinates to rigidity analysis.

17. The method of claim 1, the method further comprising, prior to the altering (B), determining the residues of the polymer that comprise the first domain, the first hinge, and the second domain by subjecting the initial set of three-dimensional coordinates to sequence feature analysis.

18. The method of claim 1, wherein the protein comprises a plurality of hinges, the plurality of hinges including the first hinge, wherein, for each respective hinge in the plurality of hinges, there is a corresponding pair of domains in the plurality of domains that pivot with respect to each other about the respective hinge, the method further comprising, prior to the altering (B), determining the identity of the residues in each hinge in the plurality of hinges by subjecting the initial set of three-dimensional coordinates to sequence feature analysis.

19. The method of claim 1 wherein the altering (B) further comprises repacking protein side chain geometries in the alternate set of three-dimensional coordinates by applying a protein packing algorithm.

20. The method of claim 19, wherein the protein packing algorithm optimizes side chain rotamer geometry for amino acids in the protein that are displaced by the altering (B).

21. The method of claim 1, wherein the potential energy function comprises a physics-based energy function.

22. The method of claim 1, wherein the potential energy function comprises a knowledge-based energy function.

23. The method of claim 1, wherein
each residue in the second plurality of residues is associated with a backbone torsion angle in a plurality of backbone torsion angles, and
the pivoting the first domain with respect to the second domain comprises biasing respective backbone torsion angles in the plurality of backbone torsion angles towards stereochemically acceptable dihedral states.

24. The method of claim 1, further comprising performing a molecular dynamics simulation of the altered set of three-dimensional coordinates prior to the scoring (C).

25. The method of claim 24, wherein the molecular dynamics simulation comprises using an explicit or implicit solvent model.

26. The method of claim 24, wherein the molecular dynamics simulation is a serial replica exchange (SRE) molecular dynamics simulation.

27. The method of claim 26, wherein the SRE molecular dynamics simulation comprises temperature tempering or solvent tempering.

28. The method of claim 1, wherein the scoring (C) comprises calculating a free energy landscape based on the altered set of three-dimensional coordinates by using a method selected from the group consisting of Umbrella Sampling, Thermodynamic Integration, Free Energy Perturbation, Adaptive Biasing Force based potential of mean force calculations and targeted molecular dynamics.

29. The method of claim 1, wherein a plurality of instances of the altering (B) is performed thereby generating a plurality of altered sets of three-dimensional coordinates.

30. The method of claim 29 wherein the protonation state of an ionizable amino acid side chain in the protein varies among the plurality of altered sets of three-dimensional coordinates.

31. The method of claim 29, further comprising assigning each altered set of three-dimensional coordinates in the plurality of altered sets of three-dimensional coordinates to one of a plurality of conformational clusters, wherein the assigning step comprises clustering based on structural data of the plurality of altered sets of three-dimensional coordinates selected from the group consisting of an inter-domain geometric parameter, an inter-atomic contact pattern, a radius of gyration, a solvent accessibility and root mean square deviation.

32. The method of claim 1, wherein a plurality of instances of the altering (B) are performed concurrently thereby obtaining a plurality of altered sets of three-dimensional coordinates for the protein, the method further comprising concurrently performing a separate independent molecular dynamics simulation of each altered set of three-dimensional coordinates in the plurality of altered sets of three-dimensional coordinates, thereby performing a plurality of independent molecular dynamics simulations, prior to the scoring (C).

33. The method of claim 32, wherein the plurality of independent molecular dynamics simulations is performed in parallel (a) on nodes of a computer cluster, (b) in a distributed computing system or (c) by general purpose computing on graphics processing units.

34. The method of claim 32, wherein, when a conformational similarity between intermediate structures in any two of the plurality of independent molecular dynamics simulations is within a predetermined threshold, one of the two molecular dynamics simulations is terminated.

35. The method of claim 32, wherein an independent molecular dynamics simulation in the plurality of independent molecular dynamics simulation comprises adaptively computing an energy distribution of a plurality of conformations of the protein.

36. The method of claim 1, wherein the altering (B) biases the altered set of three-dimensional coordinates toward a principal low frequency mode of motion using principal component analysis of a molecular dynamics trajectory or anisotropic elastic network model analysis.

37. The method of claim 1, wherein the protein is characterized by a primary sequence of residues and wherein the residues in the first hinge are from different portions of the primary sequence that are interrupted by portions of the primary sequence that are in the first domain or the second domain.

38. The method of claims 1, wherein the protein comprises thirty or more residues.

39. The method of claim 1, wherein the first hinge comprises five or more residues.

40. The method of claim 1, wherein
each residue in the second plurality of residues is associated with a backbone torsion angle in a plurality of backbone torsion angles, and
the pivoting the first domain with respect to the second domain comprises biasing respective backbone torsion angles in the plurality of backbone torsion angles towards stereochemically acceptable dihedral states, and
the protein is characterized by a primary sequence of residues and wherein the residues in the first hinge are from different portions of the primary sequence that are interrupted by portions of the primary sequence that are in the first domain or the second domain.

41. The method of claim 1, wherein
the first hinge consists of n residues, wherein n is a positive integer of two or greater,
the first hinge comprises $2(n-2)$ backbone dihedral angles,
a subset of the $2(n-2)$ backbone dihedral angles in the first hinge are not altered during the altering (B).

42. The method of claim 1, wherein the scoring (C) is performed using a knowledge-based energy function.

43. A computer system for sampling and analysis of protein conformational dynamics by searching the conformation space of a protein, the computer system comprising at least one processor and memory storing at least one program for execution by the at least one processor, the memory further comprising instructions for executing the method of claim 1.

44. A non-transitory computer readable storage medium storing one or more computational modules for sampling and analysis of protein conformational dynamics by searching the conformation space of a protein, the one or more computational modules collectively comprising instructions for performing the method of claim 1.

* * * * *